United States Patent
Barth et al.

(10) Patent No.: US 10,072,093 B2
(45) Date of Patent: Sep. 11, 2018

(54) FUSION PROTEIN TO TARGET AND TREAT ACUTE MYELOID LEUKEMIA CELLS

(71) Applicants: Fraunhofer-Gesellschaft zur Förderung der angewandten Forschung e.V., Munich (DE); Rheinisch-Westfaelische Technische Hochschule Aachen, Aachen (DE)

(72) Inventors: Stefan Barth, Munich (DE); Jenny Fitting, Aachen (DE); Mehmet Kemal Tur, Giessen (DE)

(73) Assignees: FRAUNHOFER-GESELLSCHAFT ZUR FÖRDERUNG DER ANGEWANDTEN FORSCHUNG E.V., Munich (DE); RHEINISCH-WESTFALISCHE TECHNISCHE HOCHSCHULE AACHEN, Munich (DE)

( * ) Notice: Subject to any disclaimer, the term of this patent is extended or adjusted under 35 U.S.C. 154(b) by 0 days.

(21) Appl. No.: 14/901,016

(22) PCT Filed: Jul. 4, 2014

(86) PCT No.: PCT/EP2014/064304
§ 371 (c)(1),
(2) Date: Dec. 22, 2015

(87) PCT Pub. No.: WO2015/001078
PCT Pub. Date: Jan. 8, 2015

(65) Prior Publication Data
US 2016/0152724 A1    Jun. 2, 2016

(30) Foreign Application Priority Data
Jul. 4, 2013    (EP) .................................... 13175180

(51) Int. Cl.
*C07K 16/30* (2006.01)
*C12N 9/10* (2006.01)
*G01N 33/574* (2006.01)

(52) U.S. Cl.
CPC ........ *C07K 16/3061* (2013.01); *C12N 9/1077* (2013.01); *G01N 33/57426* (2013.01); *C07K 2317/56* (2013.01); *C07K 2317/565* (2013.01); *C07K 2317/622* (2013.01); *C07K 2317/73* (2013.01); *C07K 2317/77* (2013.01); *C07K 2317/92* (2013.01); *C07K 2319/55* (2013.01); *C07K 2319/60* (2013.01); *C12Y 204/02036* (2013.01)

(58) Field of Classification Search
CPC .......... C07K 2317/622; C07K 2317/73; C07K 2317/77; C07K 2319/55; C07K 2317/56
USPC ......... 424/133.1, 178.1; 435/193; 530/387.3, 530/389.7
See application file for complete search history.

(56) References Cited

U.S. PATENT DOCUMENTS

| | | | |
|---|---|---|---|
| 4,946,778 A | 8/1990 | Ladner et al. | |
| 6,599,505 B1 * | 7/2003 | Rosenblum | A61K 39/39591 424/133.1 |
| 7,297,335 B2 * | 11/2007 | Rosenblum | A61K 39/39591 424/133.1 |
| 9,023,996 B2 * | 5/2015 | Grosse-Hovest | C07K 16/2896 435/328 |
| 9,409,995 B2 * | 8/2016 | Foord | C07K 16/30 |
| 2003/0157092 A1 * | 8/2003 | Rosenblum | A61K 39/39591 424/132.1 |
| 2008/0089898 A1 * | 4/2008 | Rosenblum | A61K 39/39591 424/183.1 |
| 2014/0105888 A1 * | 4/2014 | Foord | C07K 16/30 424/133.1 |
| 2014/0120096 A1 * | 5/2014 | Bakker | C07K 16/28 424/136.1 |
| 2016/0272723 A1 * | 9/2016 | Foord | C07K 16/30 |

FOREIGN PATENT DOCUMENTS

| | | |
|---|---|---|
| WO | WO-2007/014743 A2 | 2/2007 |
| WO | WO-2007/049044 A1 | 5/2007 |
| WO | WO-2009/013359 A2 | 1/2009 |
| WO | WO 2011076922 * | 6/2011 |
| WO | WO-2013/003625 A2 | 1/2013 |
| WO | WO-2013/006490 A2 | 1/2013 |
| WO | WO-2015/001078 | 1/2016 |

OTHER PUBLICATIONS

Fitting et al. mAbs 7:2, 390-402; Mar./Apr. 2015.*
Voskoglou-Nomikos (Clin. Can. Res. 9:4227-4239 (2003)).*
Dennis (Nature 442:739-741 (2006)).*
Cespedes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Huang et al. (Appl Microbiol Biotechnol (2010) 87:401-410).*
Fitting et al. (mAbs 7:2, 390-402; Mar./Apr. 2015).*
Mladenov et al. (Int. J. Cancer: 137, 2729-2738 (2015)).*
"Kasumi-1 cell line" (ATCC CRL-2724; pp. 1-6; Jun. 13, 2018).*
Carroll, S.F. et al., *Meth. Enzymol*, 1994, 235; 631-639.
Barbieri, L. et al., *Biochem Biophys*, 1993, Acta 1154; 237-282.
Youle, R.J. et al., *Crit. Rev. Therap. Drug Carrier Systems*, 1993, 10; 1-28.
Deonarain, M.P. et al., *Br. J. Cancer*, 1994, 70; 786-794.
Abutalib, S.A. et al., "Monoclonal antibodies for the treatment of acute myeloid leukemia," *Curr Pharm Biotechnol*, 2006, 7; 343-369.
American Cancer Society Cancer Facts & Figures 2013. http://www.cancer.org/acs/groups/content/@epidemiologysurveilance/documents/document/acspc-036845.pdf. Accession date: 2013.
Stone, R. M. "The difficult problem of acute myeloid leukemia in the older adult," *CA Cancer J Clin*, 2002, 52; 363-71.
Mulford, D. "Antibody therapy for acute myeloid leukemia," *Semin Hematol*, 2008, 45; 104-9.

(Continued)

*Primary Examiner* — Lynn A Bristol
(74) *Attorney, Agent, or Firm* — Venable, LLP; Keith G. Haddaway; Kerri M. Patterson

(57) ABSTRACT

A polypeptide which binds to the surface of AML blast cells and is internalized upon binding to the AML blast cells.

2 Claims, 5 Drawing Sheets

Specification includes a Sequence Listing.

(56) References Cited

OTHER PUBLICATIONS

Pagel, J. M. et al., "Allogeneic hematopoietic cell transplantation after conditioning with 131I-anti-CD45 antibody plus fludarabine and low-dose total body irradiation for elderly patients with advanced acute myeloid leukemia or high-risk myelodysplastic syndrome," *Blood*, 2009, 114; 5444-53.
Bunjes, D. et al., "Rhenium 188-labeled anti-CD66 (a, b, c, e) monoclonal antibody to intensify the conditioning regimen prior to stem cell transplantation for patients with high-risk acute myeloid leukemia or myelodysplastic syndrome: results of a phase I-II study," *Blood*, 2001, 98; 565-72.
Ten Cate, B. et al., "A novel AML-selective TRAIL fusion protein that is superior to Gemtuzumab Ozogamicin in terms of in vitro selectivity, activity and stability," *Leukemia*, 2009, 23; 1389-97.
Pfizer Voluntarily Withdraws Cancer Treatment Mylotarg from U.S. Market. http://www.fda.gov/NewsEvents/Newsroom/PressAnnouncements/ucm216448.htm; Accession date: Mar. 14, 2016.
Frankel, A.E. et al., "Cell surface receptor-targeted therapy of acute myeloid leukemia: a review," *Cancer Biother Radiopharm*, 2000, 15; 459-76.
Kampmeier, F. et al., "Site-Specific, Covalent Labeling of Recombinant Antibody Fragments via Fusion to an Engineered Version of 6-O-Alkylguanine DNA Alkyltransferase," *Bioconjug Chem*, 2009, 20; 1010-5.
Fitting, J. et al., "Generation of recombinant antibody fragments that target canine dendritic cells by phage display technology," *Vet Comp Oncol*, 2011, 9; 183-95.
Tur, M.K. et al., "A novel approach for immunization, screening and characterization of selected scFv libraries using membrane fractions of tumor cells," *Int J Mol Med*, 2003, 11; 523-7.
Stocker, M. et. al., "Secretion of functional anti-CD30-angiogenin immunotoxins into the supernatant of transfected 293T-cells," *Protein Expr Purif*, 2003, 28; 211-9.
Benedict, C.A. et al., "Determination of the binding affinity of an anti-CD34 single-chain antibody using a novel, flow cytometry based assay," *J Immunol Methods*, 1997, 201; 223-31.
Tur, M.K. et al., "Recombinant CD64-specific single chain immunotoxin exhibits specific cytotoxicity against acute myeloid leukemia cells," *Cancer Res*, 2003, 63; 8414-9.
Barth, S. et al., "Compatible-solute-supported periplasmic expression of functional recombinant proteins under stress conditions," *Appl Environ Microbiol*, 2000, 66; 1572-9.
Barth, S. et al., "Ki-4(scFv)-ETA', a new recombinant anti-CD30 immunotoxin with highly specific cytotoxic activity against disseminated Hodgkin tumors in SCID mice," *Blood*, 2000, 95; 3909-14.
Tur, M.K. et al., "Immunokinases, a novel class of immunotherapeutics for targeted cancer therapy," *Curr Pharm Des*, 2009, 15; 2693-9.
Kabat, E.A. et al., "Identical V region amino acid sequences and segments of sequences in antibodies of different specificities. Relative contributions of VH and VL genes, minigenes, and complementarity-determining regions to binding of antibody-combining sites," *J Immunol*, 1991, 147; 1709-19.

Arnold, K. et al., "The Swiss-Model workspace: a web-based environment for protein structure homology modelling," *Bioinformatics*, 2005, 22; 195-201.
Schwede, T. et al., "Swiss-Model: An automated protein homology-modeling server," *Nucleic Acids*, 2003, Res 31; 3381-5.
Guex, N. et al., "Swiss-Model and the Swiss-PdbViewer: an environment for comparative protein modeling," *Electrophoresis*, 1997, 18; 2714-23.
Chothia, C. et al., "Canonical structures for the hypervariable regions of immunoglobulins," *J Mol Biol*, 1987, 196; 901-17.
Chothia, C. et al., "Conformations of immunoglobulin hypervariable regions," *Nature*, 1989, 342; 877-83.
Stone, R.M. et al., "Acute myeloid leukemia," *Hematology Am Soc Hematol Educ Program*, 2004, 98-117.
Tallman, M.S. "New strategies for the treatment of acute myeloid leukemia including antibodies and other novel agents," *Hematology Am Soc Hematol Educ Program*, 2005, 143-50.
Khandare, J.J. et al., "Antibodies and peptides in cancer therapy," *Crit Rev Ther Drug Carrier Syst*, 2006, 23; 401-35.
Becerril, B. et al., "Toward selection of internalizing antibodies from phage libraries," *Biochem Biophys Res Commun*, 1999, 255; 386-93.
Barth, S. et al., "Immunotoxins. Mechanism of action and applications in malignant diseases," *Internist (Berl)*, 1997, 38;1063-9.
Hetzel, C. et al., "Improved immunotoxins with novel functional elements," *Curr Pharm Des*, 2009, 15; 2700-11.
Stish, B.J. et al., "Increasing anticarcinoma activity of an anti-erbB2 recombinant immunotoxin by the addition of an anti-EpCAM sFv," *Clin Cancer Res*, 2007, 13; 3058-67.
Schmidt, M.M. et al., "Kinetics of anti-carcinoembryonic antigen antibody internalization: effects of affinity, bivalency, and stability," *Cancer Immunol Immunother*, 2008, 57; 1879-90.
Hetzel, C. et al., "Small cleavable adapters enhance the specific cytotoxicity of a humanized immunotoxin directed against CD64-positive cells," *J Immunother*, 2008, 31; 370-6.
Stahnke, B. et al., "Granzyme B-H22(scFv), a human immunotoxin targeting CD64 in acute myeloid leukemia of monocytic subtypes," *Mol Cancer Ther*, 2008, 7; 2924-32.
Tur, M. K. et all., "In vivo efficacy of the recombinant anti-CD64 immunotoxin H22(scFv)-ETA' in a human acute myeloid leukemia xenograft tumor model," *International Journal of Cancer*, 2011, 129, 1277-1282.
Stein, C. et al., "Novel conjugates of single-chain Fv antibody fragments specific for stem cell antigen CD123 mediate potent death of acute myeloid leukaemia cells," *British Journal of Haematology*, 2010, 148, 879-889.
Cravens et al., "Human Peripheral Blood Dendritic Cells and Monocyte Subsets Display Similar Chemokine Receptor Expression Profiles with Differential Migratory Responses," Scandinavian Journal of Immunology, 65, pp. 514-524 (2007).
Tanaka et al., "Activation of FcγR1 on monocytes triggers differentiation into immature dendritic cells that induce autoreactive T cell responses," J. Immunol. 183(4): 2349-2355 (2009).
Yu et al., "Human BDCA2$^+$CD123$^+$CD56$^+$ dendritic cells (DCs) related to blastic plasmacytoid dendritic cell neoplasm represent a unique myeloid DC subset," Protein Cell, 6(4): 297-306 (2015).

* cited by examiner

```
                        SEQUENCE LISTING

<160> NUMBER OF SEQ ID NOS: 43

<210> SEQ ID NO 1
<211> LENGTH: 5
<212> TYPE: PRT
<213> ORGANISM: artificial
<220> FEATURE:
<223> OTHER INFORMATION: CDR1 of heavy chain of antibody structure

<400> SEQUENCE: 1

Ser Tyr Ala Met Ser
1               5

<210> SEQ ID NO 2
<211> LENGTH: 17
<212> TYPE: PRT
<213> ORGANISM: artificial
<220> FEATURE:
<223> OTHER INFORMATION: CDR2 of heavy chain of antibody structur

<400> SEQUENCE: 2

Ala Ile Gly Val Gln Gly Asp Arg Thr Ala Tyr Ala Asp Ser Val Lys
1               5                   10                  15

Gly

<210> SEQ ID NO 3
<211> LENGTH: 17
<212> TYPE: PRT
<213> ORGANISM: artificial
<220> FEATURE:
<223> OTHER INFORMATION: CDR2 of heavy chain of antibody structure

<400> SEQUENCE: 3

Ile Ile Gln Pro Thr Gly Arg Lys Thr Thr Tyr Ala Asp Ser Val Lys
1               5                   10                  15

Gly

<210> SEQ ID NO 4
<211> LENGTH: 17
<212> TYPE: PRT
```

```
<213> ORGANISM: artificial
<220> FEATURE:
<223> OTHER INFORMATION: CDR2 of heavy chain of antibody structure

<400> SEQUENCE: 4

Thr Ile Gln Gln Tyr Gly Thr Pro Thr Trp Tyr Ala Asp Ser Val Lys
1               5                   10                  15
Gly

<210> SEQ ID NO 5
<211> LENGTH: 17
<212> TYPE: PRT
<213> ORGANISM: artificial
<220> FEATURE:
<223> OTHER INFORMATION: CDR2 of heavy chain of antibody structure

<400> SEQUENCE: 5

Thr Ile Ala Gln Lys Gly Leu Arg Thr Ala Tyr Ala Asp Ser Val His
1               5                   10                  15
Gly

<210> SEQ ID NO 6
<211> LENGTH: 17
<212> TYPE: PRT
<213> ORGANISM: artificial
<220> FEATURE:
<223> OTHER INFORMATION: CDR2 of heavy chain of antibody structure

<400> SEQUENCE: 6

Ala Ile Gln Gln Arg Gly Leu Lys Thr Ala Tyr Ala Asp Ser Val Lys
1               5                   10                  15
Gly

<210> SEQ ID NO 7
<211> LENGTH: 17
<212> TYPE: PRT
<213> ORGANISM: artificial
<220> FEATURE:
<223> OTHER INFORMATION: CDR2 of heavy chain of antibody structure

<400> SEQUENCE: 7

Thr Ile Gln Lys Leu Gly Arg Gln Thr Ala Tyr Ala Asp Ser Val Lys
1               5                   10                  15
Gly

<210> SEQ ID NO 8
<211> LENGTH: 7
<212> TYPE: PRT
<213> ORGANISM: artificial
<220> FEATURE:
<223> OTHER INFORMATION: CDR3 of heavy chain of antibody structure

<400> SEQUENCE: 8

Gly Ile Arg Ala Phe Asp Tyr
1               5

<210> SEQ ID NO 9
<211> LENGTH: 7
<212> TYPE: PRT
<213> ORGANISM: artificial
<220> FEATURE:
<223> OTHER INFORMATION: CDR3 of heavy chain of antibody structure

<400> SEQUENCE: 9
```

```
Ser Ser Tyr Met Phe Asp Tyr
1               5

<210> SEQ ID NO 10
<211> LENGTH: 7
<212> TYPE: PRT
<213> ORGANISM: artificial
<220> FEATURE:
<223> OTHER INFORMATION: CDR3 of heavy chain of antibody structure

<400> SEQUENCE: 10

Ser Tyr Pro Ser Phe Asp Tyr
1               5

<210> SEQ ID NO 11
<211> LENGTH: 7
<212> TYPE: PRT
<213> ORGANISM: artificial
<220> FEATURE:
<223> OTHER INFORMATION: CDR3 of heavy chain of antibody structure

<400> SEQUENCE: 11

Arg Leu Ser Val Phe Asp Tyr
1               5

<210> SEQ ID NO 12
<211> LENGTH: 7
<212> TYPE: PRT
<213> ORGANISM: artificial
<220> FEATURE:
<223> OTHER INFORMATION: CDR3 of heavy chain of antibody structure

<400> SEQUENCE: 12

Gly Trp Arg Arg Phe Asp Tyr
1               5

<210> SEQ ID NO 13
<211> LENGTH: 11
<212> TYPE: PRT
<213> ORGANISM: artificial
<220> FEATURE:
<223> OTHER INFORMATION: CDR1 of light chain of antibody structure

<400> SEQUENCE: 13

Arg Ala Ser Gln Ser Ile Ser Ser Tyr Leu Asn
1               5                   10

<210> SEQ ID NO 14
<211> LENGTH: 7
<212> TYPE: PRT
<213> ORGANISM: artificial
<220> FEATURE:
<223> OTHER INFORMATION: CDR2 of light chain of antibody structure

<400> SEQUENCE: 14

Ala Ala Ser Ser Leu Gln Ser
1               5

<210> SEQ ID NO 15
<211> LENGTH: 7
<212> TYPE: PRT
<213> ORGANISM: artificial
<220> FEATURE:
<223> OTHER INFORMATION: CDR2 of light chain of antibody structure

<400> SEQUENCE: 15

Ser Ala Ser Ala Leu Gln Ser
```

```
1               5

<210> SEQ ID NO 16
<211> LENGTH: 7
<212> TYPE: PRT
<213> ORGANISM: artificial
<220> FEATURE:
<223> OTHER INFORMATION: CDR2 of light chain of antibody structure

<400> SEQUENCE: 16

Lys Ala Ser Leu Leu Gln Ser
1               5

<210> SEQ ID NO 17
<211> LENGTH: 7
<212> TYPE: PRT
<213> ORGANISM: artificial
<220> FEATURE:
<223> OTHER INFORMATION: CDR2 of light chain of antibody structure

<400> SEQUENCE: 17

Arg Ala Ser Ile Leu Gln Ser
1               5

<210> SEQ ID NO 18
<211> LENGTH: 7
<212> TYPE: PRT
<213> ORGANISM: artificial
<220> FEATURE:
<223> OTHER INFORMATION: CDR2 of light chain of antibody structure

<400> SEQUENCE: 18

Asn Ala Ser His Leu Gln Ser
1               5

<210> SEQ ID NO 19
<211> LENGTH: 7
<212> TYPE: PRT
<213> ORGANISM: artificial
<220> FEATURE:
<223> OTHER INFORMATION: CDR2 of light chain of antibody structure

<400> SEQUENCE: 19

Lys Ala Ser Leu Leu Gln Ser
1               5

<210> SEQ ID NO 20
<211> LENGTH: 9
<212> TYPE: PRT
<213> ORGANISM: artificial
<220> FEATURE:
<223> OTHER INFORMATION: CDR3 of light chain of antibody structure

<400> SEQUENCE: 20

Gln Gln Tyr Ala Gly Ala Pro Ser Thr
1               5

<210> SEQ ID NO 21
<211> LENGTH: 9
<212> TYPE: PRT
<213> ORGANISM: artificial
<220> FEATURE:
<223> OTHER INFORMATION: CDR3 of light chain of antibody structure

<400> SEQUENCE: 21

Gln Gln Ala Arg Arg Arg Pro Leu Thr
1               5
```

<210> SEQ ID NO 22
<211> LENGTH: 9
<212> TYPE: PRT
<213> ORGANISM: artificial
<220> FEATURE:
<223> OTHER INFORMATION: CDR3 of light chain of antibody structure

<400> SEQUENCE: 22

Gln Gln Pro Arg Val Leu Pro Leu Thr
1               5

<210> SEQ ID NO 23
<211> LENGTH: 9
<212> TYPE: PRT
<213> ORGANISM: artificial
<220> FEATURE:
<223> OTHER INFORMATION: CDR3 of light chain of antibody structure

<400> SEQUENCE: 23

Gln Gln Ala Tyr Lys Gly Pro Leu Thr
1               5

<210> SEQ ID NO 24
<211> LENGTH: 9
<212> TYPE: PRT
<213> ORGANISM: artificial
<220> FEATURE:
<223> OTHER INFORMATION: CDR3 of light chain of antibody structure

<400> SEQUENCE: 24

Gln Gln Arg Gly His Asn Pro Val Thr
1               5

<210> SEQ ID NO 25
<211> LENGTH: 9
<212> TYPE: PRT
<213> ORGANISM: artificial
<220> FEATURE:
<223> OTHER INFORMATION: CDR3 of light chain of antibody structure

<400> SEQUENCE: 25

Gln Gln Gly Arg Leu Pro Pro Pro Thr
1               5

<210> SEQ ID NO 26
<211> LENGTH: 9
<212> TYPE: PRT
<213> ORGANISM: artificial
<220> FEATURE:
<223> OTHER INFORMATION: CDR3 of light chain of antibody structure

<400> SEQUENCE: 26

Gln Gln Ser Gln Thr Ala Pro Leu Thr
1               5

<210> SEQ ID NO 27
<211> LENGTH: 117
<212> TYPE: PRT
<213> ORGANISM: artificial
<220> FEATURE:
<223> OTHER INFORMATION: heavy chain of antibody

<400> SEQUENCE: 27

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
            35                  40                  45

Trp Val Ser Ala Ile Gly Val Gln Gly Asp Arg Thr Ala Tyr Ala Asp
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Asp Thr Ala Val Tyr
                    85                  90                  95

Tyr Cys Ala Lys Gly Ile Arg Ala Phe Asp Tyr Trp Gly Gln Gly Thr
            100                 105                 110

Leu Val Thr Val Ser
        115

<210> SEQ ID NO 28
<211> LENGTH: 117
<212> TYPE: PRT
<213> ORGANISM: artificial
<220> FEATURE:
<223> OTHER INFORMATION: heavy chain of antibody

<400> SEQUENCE: 28

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
            35                  40                  45

Trp Val Ser Ile Ile Gln Pro Thr Gly Arg Lys Thr Thr Tyr Ala Asp
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                    85                  90                  95

Tyr Cys Ala Lys Ser Ser Tyr Met Phe Asp Tyr Trp Gly Gln Gly Thr
            100                 105                 110

Leu Val Thr Val Ser
        115

<210> SEQ ID NO 29
<211> LENGTH: 117
<212> TYPE: PRT
<213> ORGANISM: artificial
<220> FEATURE:
<223> OTHER INFORMATION: heavy chain of antibody

<400> SEQUENCE: 29

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
            35                  40                  45

Trp Val Ser Thr Ile Gln Gln Tyr Gly Thr Pro Thr Trp Tyr Ala Asp
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                85                  90                  95

Tyr Cys Ala Lys Ser Tyr Pro Ser Phe Asp Tyr Trp Gly Gln Gly Thr
            100                 105                 110

Leu Val Thr Val Ser
        115

<210> SEQ ID NO 30
<211> LENGTH: 117
<212> TYPE: PRT
<213> ORGANISM: artificial
<220> FEATURE:
<223> OTHER INFORMATION: heavy chain of antibody

<400> SEQUENCE: 30

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Thr Ile Ala Gln Lys Gly Leu Arg Thr Ala Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Arg Leu Ser Val Phe Asp Tyr Trp Gly Gln Gly Thr
            100                 105                 110

Leu Val Thr Val Ser
        115

<210> SEQ ID NO 31
<211> LENGTH: 117
<212> TYPE: PRT
<213> ORGANISM: artificial
<220> FEATURE:
<223> OTHER INFORMATION: heavy chain of antibody

<400> SEQUENCE: 31

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ala Ile Gln Gln Arg Gly Leu Lys Thr Ala Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Gly Trp Arg Arg Phe Asp Tyr Trp Gly Gln Gly Thr
            100                 105                 110

Leu Val Thr Val Ser
        115

```
<210> SEQ ID NO 32
<211> LENGTH: 117
<212> TYPE: PRT
<213> ORGANISM: artificial
<220> FEATURE:
<223> OTHER INFORMATION: heavy chain of antibody

<400> SEQUENCE: 32

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Thr Ile Gln Lys Leu Gly Arg Gln Thr Ala Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Ser Ala Arg Arg Phe Asp Tyr Trp Gly Gln Gly Thr
            100                 105                 110

Leu Val Thr Val Ser
        115

<210> SEQ ID NO 33
<211> LENGTH: 117
<212> TYPE: PRT
<213> ORGANISM: artificial
<220> FEATURE:
<223> OTHER INFORMATION: heavy chain of antibody

<400> SEQUENCE: 33

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Thr Ile Gln Lys Leu Gly Arg Gln Thr Ala Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Ser Ala Arg Arg Phe Asp Tyr Trp Gly Gln Gly Thr
            100                 105                 110

Leu Val Thr Val Ser
        115

<210> SEQ ID NO 34
<211> LENGTH: 109
<212> TYPE: PRT
<213> ORGANISM: artificial
<220> FEATURE:
<223> OTHER INFORMATION: light chain of antibody

<400> SEQUENCE: 34

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ala Gly Ala Pro Ser
                85                  90                  95

Thr Phe Gly Gln Gly Thr Lys Val Glu Ile Lys Arg Ala
            100                 105

<210> SEQ ID NO 35
<211> LENGTH: 109
<212> TYPE: PRT
<213> ORGANISM: artificial
<220> FEATURE:
<223> OTHER INFORMATION: light chain of antibody

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ser Ala Ser Ala Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Arg Arg Arg Pro Leu
                85                  90                  95

Thr Phe Gly Gln Gly Thr Lys Val Glu Ile Lys Arg Ala
            100                 105

<210> SEQ ID NO 36
<211> LENGTH: 109
<212> TYPE: PRT
<213> ORGANISM: artificial
<220> FEATURE:
<223> OTHER INFORMATION: light chain of antibody

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Lys Ala Ser Leu Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Arg Val Leu Pro Leu
                85                  90                  95

Thr Phe Gly Gln Gly Thr Lys Val Glu Ile Lys Arg Ala

<210> SEQ ID NO 37
<211> LENGTH: 109
<212> TYPE: PRT
<213> ORGANISM: artificial
<220> FEATURE:
<223> OTHER INFORMATION: light chain of antibody

<400> SEQUENCE: 37

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Lys Gly Pro Leu
                85                  90                  95

Thr Phe Gly Gln Gly Thr Lys Val Glu Ile Lys Arg Ala
            100                 105
```

<210> SEQ ID NO 38
<211> LENGTH: 109
<212> TYPE: PRT
<213> ORGANISM: artificial
<220> FEATURE:
<223> OTHER INFORMATION: light chain of antibody

<400> SEQUENCE: 38

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Asn Ala Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Gly His Asn Pro Val
                85                  90                  95

Thr Phe Gly Gln Gly Thr Lys Val Glu Ile Lys Arg Ala
            100                 105
```

<210> SEQ ID NO 39
<211> LENGTH: 109
<212> TYPE: PRT
<213> ORGANISM: artificial
<220> FEATURE:
<223> OTHER INFORMATION: light chain of antibody

<400> SEQUENCE: 39

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30
```

Leu Asn Trp Tyr Gln Gln Lys Pro Gly Lys Ala Pro Lys Leu Leu Ile
            35                  40                  45

Tyr Lys Ala Ser Leu Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Arg Leu Pro Pro Pro
                85                  90                  95

Thr Phe Gly Gln Gly Thr Lys Val Glu Ile Lys Arg Ala
            100                 105

<210> SEQ ID NO 40
<211> LENGTH: 109
<212> TYPE: PRT
<213> ORGANISM: artificial
<220> FEATURE:
<223> OTHER INFORMATION: light chain of antibody

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Lys Ala Ser Leu Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gln Thr Ala Pro Leu
                85                  90                  95

Thr Phe Gly Gln Gly Thr Lys Val Glu Ile Lys Arg Ala
            100                 105

<210> SEQ ID NO 41
<211> LENGTH: 17
<212> TYPE: DNA
<213> ORGANISM: artificial
<220> FEATURE:
<223> OTHER INFORMATION: Primer LMB3

<400> SEQUENCE: 41
caggaaacag ctatgac                                                17

<210> SEQ ID NO 42
<211> LENGTH: 17
<212> TYPE: DNA
<213> ORGANISM: artificial
<220> FEATURE:
<223> OTHER INFORMATION: Primer fdSEQ1

<400> SEQUENCE: 42
gaattttctg tatgagg                                                17

<210> SEQ ID NO 43
<211> LENGTH: 614
<212> TYPE: PRT
<213> ORGANISM: artificial
<220> FEATURE:
<223> OTHER INFORMATION: fusion polypeptide comprising ETA

<400> SEQUENCE: 43

```
Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ala Ile Gln Gln Arg Gly Leu Lys Thr Ala Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Gly Trp Arg Arg Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Thr Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Asn Ala Ser His Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Arg Gly His Asn Pro Val Thr Phe Gly Gln Gly Thr Lys Val Glu Ile
225                 230                 235                 240

Lys Arg Ala Ala Ala Glu Leu Ala Ser Gly Gly Pro Glu Gly Gly Ser
                245                 250                 255

Leu Ala Ala Leu Thr Ala His Gln Ala Cys His Leu Pro Leu Glu Thr
            260                 265                 270

Phe Thr Arg His Arg Gln Pro Arg Gly Trp Glu Gln Leu Glu Gln Cys
        275                 280                 285

Gly Tyr Pro Val Gln Arg Leu Val Ala Leu Tyr Leu Ala Ala Arg Leu
    290                 295                 300

Ser Trp Asn Gln Val Asp Gln Val Ile Arg Asn Ala Leu Ala Ser Pro
305                 310                 315                 320

Gly Ser Gly Gly Asp Leu Gly Glu Ala Ile Arg Glu Gln Pro Glu Gln
                325                 330                 335

Ala Arg Leu Ala Leu Thr Leu Ala Ala Ala Glu Ser Glu Arg Phe Val
            340                 345                 350

Arg Gln Gly Thr Gly Asn Asp Glu Ala Gly Ala Ala Asn Ala Asp Val
        355                 360                 365

Val Ser Leu Thr Cys Pro Val Ala Ala Gly Glu Cys Ala Gly Pro Ala
    370                 375                 380

Asp Ser Gly Asp Ala Leu Leu Glu Arg Asn Tyr Pro Thr Gly Ala Glu
385                 390                 395                 400

Phe Leu Gly Asp Gly Gly Asp Val Ser Phe Ser Thr Arg Gly Thr Gln
                405                 410                 415
```

-continued

```
Asn Trp Thr Val Glu Arg Leu Leu Gln Ala His Arg Gln Leu Glu Glu
            420                 425                 430

Arg Gly Tyr Val Phe Val Gly Tyr His Gly Thr Phe Leu Glu Ala Ala
        435                 440                 445

Gln Ser Ile Val Phe Gly Gly Val Arg Ala Arg Ser Gln Asp Leu Asp
    450                 455                 460

Ala Ile Trp Arg Gly Phe Tyr Ile Ala Gly Asp Pro Ala Leu Ala Tyr
465                 470                 475                 480

Ala Tyr Ala Gln Asp Gln Glu Pro Asp Ala Arg Gly Arg Ile Arg Asn
                485                 490                 495

Gly Ala Leu Leu Arg Val Tyr Val Pro Arg Ser Ser Leu Pro Gly Phe
            500                 505                 510

Tyr Arg Thr Ser Leu Thr Leu Ala Ala Pro Glu Ala Ala Gly Glu Val
            515                 520                 525

Glu Arg Leu Ile Gly His Pro Leu Pro Leu Arg Leu Asp Ala Ile Thr
    530                 535                 540

Gly Pro Glu Glu Glu Gly Gly Arg Leu Glu Thr Ile Leu Gly Trp Pro
545                 550                 555                 560

Leu Ala Glu Arg Thr Val Val Ile Pro Ser Ala Ile Pro Thr Asp Pro
                565                 570                 575

Arg Asn Val Gly Gly Asp Leu Asp Pro Ser Ser Ile Pro Asp Lys Glu
            580                 585                 590

Gln Ala Ile Ser Ala Leu Pro Asp Tyr Ala Ser Gln Pro Gly Lys Pro
            595                 600                 605

Pro Arg Glu Asp Leu Lys
    610
```

FUSION PROTEIN TO TARGET AND TREAT ACUTE MYELOID LEUKEMIA CELLS

CROSS-REFERENCE TO RELATED APPLICATION

This application is a U.S. National Phase of International Application No. PCT/EP2014/064304, filed Jul. 4, 2014, which claims priority to European Application No. 13175180.2, filed Jul. 4, 2013, the entire contents of each are incorporated by reference herein.

SEQUENCE LISTING

This application contains a Sequence Listing which has been submitted electronically in ASCII format and is incorporated by reference in its entirety. Said ASCII copy, created 4 Jul. 2013, is named 393850SequenceListing.txt and is 26 KB in size. Said ASCII copy is a copy of the sequence listing filed with International Application No. PCT/EP2014/064304, filed 4 Jul. 2014.

Subject matter of the present invention is a polypeptide, a compound comprising the polypeptide of the invention, the pharmaceutical composition comprising the compound of the invention, a therapeutic and diagnostic use of the compound or polypeptide of the invention as well as a method for manufacturing the polypeptide of the invention.

Acute myeloid leukemias (AML) are a heterogeneous group of hematologic disorders characterized by an uncontrolled overproduction of hematopoietic precursor cells with an inefficient activation of the apoptotic program leading to their accumulation in peripheral blood and bone marrow[1]. The American Cancer Society was estimating 14,590 cases of newly diagnosed AML and 10,370 AML-related deaths in 2013[2]. The median age at diagnosis is 65 years, which implies a dramatic rise of AML incidences in the coming years due to increased life expectancy and the resulting demographic changes[3]. The current prognosis is poor with a five-year relative survival rate of only 24%[2]. The majority of patients still die of their disease because of both treatment-associated mortality and relapse caused by blast cells surviving complete remission[1]. To control this minimal residual disease, current research is analysing the lineage-specific antigen expression on AML cells which may be exploited for specific targeting using monoclonal antibodies[4]. Several specific binders were developed against leukemia-associated antigens, such as CD45[5], a pan-leukocyte antigen, and CD66[6], a glycoprotein found on mature myeloid cells. Since single agents revealed only marginal effects, they were coupled to radionuclides to create radio-immunoconjugates. Their use is currently under investigation in clinical phase I and II trials, where they are administered prior to allogeneic stem cell transplantation. Apart from these developments, most of the attention is still focussed on the calicheamicin-coupled CD33 targeting antibody Gemtuzumab (Mylotarg). The immunoconjugate was approved by the FDA in 2000 for the treatment of patients 60 years and older with recurrent AML who were not considered candidates for standard chemotherapy[7] and withdrawn in 2010 due to a higher number of deaths in patients treated[8]. The main drawback of the mentioned target antigens is that they are not exclusively expressed on the surface of AML-cells but rather also on normal cells[9], leading to an undesired toxicity profile with severe side effects.

Current standard treatment for acute myeloid leukemia (AML) is a high dose chemotherapy based on cytarabine and daunorubicine (7+3), which poorly discriminates between malignant and benign cells. Dose limiting off-target effects as well as intrinsical drug resistance result in inefficient eradication of leukemic blast cells and their survival beyond remission. This minimal residual disease is the major cause of relapse and finally results in a five-year survival rate of only 24%.

Thus, there is a veritable need for highly specific and efficient eradication of malignant cells leaving healthy cells unaffected. One object of the present invention is therefore to provide a medicament which is able to achieve the above-mentioned aims and to avoid the drawbacks of the methods of treatment employed up to date.

WO 2013/006490 A2 discloses antibodies specific for TIM3 that can be used to detect cancer cells, in particular, cancer stem cells. The antibodies can also be used in therapeutic compositions for treating cancer and reducing inflammation.

WO 2013/003625 A2 discloses antibodies which bind to the ADP-ribosyl cyclase 2. Nucleic acid molecules encoding the antibodies, expression vectors, host cells and methods for expressing the antibodies are also provided. The antibodies may be used for the treatment of human cancers, including acute myeloid leukemia (AML), B-cell chronic lymphocytic leukemia, breast cancer, colorectal cancer, kidney cancer, head and neck cancer, lung cancer, ovarian cancer and pancreatic cancer and human inflammatory diseases, including asthma, gout, crohns, lupus, multiple sclerosis, rheumatoid arthritis, psoriasis, diabetes and atherosclerotic.

WO 2007/049044 A1 discloses agents capable of binding sialic acid-binding immunoglobulin-like lectin-9 (Siglec-9) and their use in the treatment of cell proliferation and differentiation disorders. Furthermore, the present invention provides associated pharmaceutical formulations and methods.

The invention is based on the discovery that one scFv fused to a truncated form of *Pseudomonas* exotoxin A (ETA') results in a recombinant immunotoxin (IT) and effecting AML-selective inhibition of cell proliferation and induction of apoptosis.

SUMMARY OF THE INVENTION

The object of the invention is accomplished by a polypeptide which binds to the surface of AML blast cells and is internalised upon binding to the AML blast cells.

The polypeptide comprises an antibody or antibody fragment comprising an amino acid sequence wherein the polypeptide is corresponding to the complementarity determining regions (CDRs) CDR1, CDR2 and CDR3 of the heavy chain of the variable region of an antibody $v_H$ having the amino acid sequences for CDR1: comprising a stretch of 2 polar neutral amino acids, followed by 2 nonpolar neutral amino acids, and followed by a polar neutral amino acid;

CDR2 comprising a stretch of 10 amino acids which comprises 2 polar amino acids each with a positive side chain, one polar amino acid with a negative side chain and 1 proline which stretch is linked to a further stretch comprising a polar neutral amino acid, followed by a nonpolar neutral amino acid, followed by a polar amino acid having a negatively charged side chain, followed by a polar neutral amino acid, followed by a nonpolar neutral amino acid followed by a polar amino acid having a positively charged side chain, followed by a nonpolar neutral amino acid;

CDR3 comprising a stretch of 7 amino acids wherein the 5th amino acid is nonpolar neutral, followed by a polar amino acid having a negatively charged side chain, followed by a 7$^{th}$ amino acid which is polar neutral.

In another embodiment of the invention, the N-terminal of the polypeptide is comprising 20 to 35 amino acids linked to the CDR1 which is followed by a stretch of 8 to 15 amino acids followed by CDR2 which is followed by a stretch of 20 to 35 amino acids which is linked to CDR3 followed by a stretch of 5 to 15 amino acids at the C-terminal and of the polypeptide.

In still another embodiment of the invention in the poly-peptide comprises an antibody or antibody fragment comprising an amino acid sequence wherein the poly-peptide is corresponding to the complementarity determining regions CDR1, CDR2 and CDR3 of the light chain of the variable region of an antibody $v_L$ having the amino acid sequences for CDR1 comprising a polar amino acid with a positively charged side chain, followed by a neutral amino acid, followed by a stretch of three polar neutral amino acids, followed by a nonpolar amino acid, followed by another stretch of three polar amino acids followed by a nonpolar amino acid and followed by polar amino acid;

CDR2 comprising a stretch of 4 amino acids comprising 2 polar amino acids the stretch of 4 amino acids followed by a nonpolar neutral amino acid, followed by 2 polar neutral amino acids; and CDR3 comprising stretch of 9 amino acids consisting of 2 polar neutral aminoacids, followed by a stretch of 4 amino acids which is followed by proline, followed by a neutral amino acid as eighth amino acid and followed by a polar neutral amino acid.

In yet another embodiment of the invention the N-terminal of the polypeptide is comprising 15 to 30 amino acids linked to the CDR1 which is followed by a stretch of 10 to 20 amino acids followed by CDR2 which is followed by a stretch of 20 to 35 amino acids which is linked to CDR3 followed by a stretch of 7 to 18 amino acids at the C-terminal and of the polypeptide.

In a further embodiment of the invention the polypeptide corresponding to the heavy chain of an antibody structure comprises 4 CDR1 the amino acid sequence of SEQ ID NO 1, comprises for CDR2 the amino acid sequence of one of the SEQ ID NOs 2 to 7, and for CDR3 comprises the amino acid sequence of one of the SEQ ID NOs 8 to 12.

In another embodiment CDR1 of the polypeptide of the invention comprises the amino acid sequence SEQ ID NO 13, the CDR2 comprises the amino acid sequence of one of the SEQ ID NOs 14 to 19, and CDR3 comprises the amino acid sequence of one of the SEQ ID NOs 20 to 26.

In yet another embodiment the polypeptide of the invention corresponding to the heavy chain of the variable region of an antibody $v_H$ comprises the amino acid sequence of one of the SEQ ID NOs 27 to 33.

In still another embodiment of the polypeptide of the invention corresponding to the light chain of the variable region of an antibody $v_L$ comprises the amino acid sequence of one of the SEQ ID NOs 34 to 40.

In a further embodiment of the polypeptide of the invention the CDR1, CDR2 and CDR3 of the heavy chain of the variable region of an antibody $v_H$ and CDR1, CDR2 and CDR3 of the light chain of the variable region of an antibody $v_L$ are linked with each other via a linker structure. Typically, according to the invention the linker structure is (Gly$_4$Ser)$_3$ The polypeptide of the invention can also show a homology of at least 90%, in particular 95%, to the amino acid sequence defining the polypeptide of the invention.

In particular the polypeptide of the invention is a recombinant antibody more specifically a single-chain variable fragment (scFv).

Subject matter of the present invention is also a compound comprising a domain comprising the polypeptide of the invention and a cytotoxic domain.

In particular the cytotoxic domain of the compound of the invention comprises at least one structural element of a molecule which element exhibits a cytotoxic or cell killing activity.

In a further embodiment of the invention the cytotoxic domain of the compound of the invention is the cytotoxic element derived from a molecule or the molecule itself which molecule is selected from the group consisting of ADP-ribosylating enzymes, such as the *Pseudomonas* Exotoxin A, Diphtheria-, Cholera- or the Pertussis-, Botulinum toxin, or a member of the ribosome-inactivating proteins such as Dianthin, Saporin, Bryodin, Gelonin, Ricin, Abrin, Pokeweed Antiviral Protein (PAP) or Restrictocin, or is a member of the RNases (Phosphodiesterases) such as the Bovine seminal RNase, Bovine RNase A, Bovine pancreatic RNase, Angiogenin, Eosinophil-derived Neurotoxin (EDN), Eosinophilic Cationic Protein (ECP), Onconase, or Bullfrog Lectin, or is a member of the Prodrug-activating enzymes such as Calicheamicin, Glucose Oxidase, Carboxypeptidase, Alkaline Phosphatase, Cytosine Deaminase, beta-Glucosidase, beta-Glucuronidase, beta-Lactamase, Nitroreductase, Thymidine Kinase or Purine Nucleoside Phosphorylase, or is a member of the serine, serine/threonine or cathepsin protease family, or a member of the calpains, or a member of the granzymes, in particular granzym B und granzym M, tumor suppressor-like kinases in particular death-associated protein kinases including DAPK 1 und 2, or microtubule-associated protein (MAP Tau), or any derivative of the above mentioned proteins, or a combination thereof.

For the coupling the cytotoxic domain and the polypeptide domain a chemical linking group can be arranged between the cytotoxic domain and the domain comprising the polypeptide of the invention. The linking of the cytotoxic domain or the detectable label can be performed by conjugation of the respective moieties with the peptide of the invention. It is also possible to use the technology as provided by the disclosure of WO2009/013359 incorporated by reference.

The great potential of the SNAP-tag technology lies within its broad range of in vitro and in vivo applications. It can be used for coupling of proteins to soluble molecules or surfaces, imaging techniques, analysis of protein-protein interaction or of pharmacokinetics in mice. Due to its versatility, a high impact of further research in the field of development of new therapeutics and diagnostics can reasonably assumed for the SNAP-tag.

Subject matter of the present invention is also a diagnostic label. According to the invention the detectable label is selected from the group consisting of fluorescent dyes, such as fluorescein, rhodamine, coumarine, and cyanine and derivatives thereof; gamma ray emitting radioisotopes as e.g. iodine-131, lutetium-177, yttrium 90 or any other diagnostically relevant isotope; a quantum dot composed of heavy metals, in particular CdSe or InGaP; noble metal nanoclusters composed of a few (8-12) gold or silver atoms, or synthetic fluorophores captured in nanoparticles made from silicon dixode; superparamagnetic iron oxid particles for MRI based molecular imaging; fluorescent proteins like GFP or dsRED or derivatives thereof; enzymes like alkaline phosphatase, peroxidases and galactosidases.

Subject matter of the present invention is also a pharmaceutical composition comprising the compound of the invention. The compound of the invention can be used in diagnosis and treatment of AML.

DETAILED DESCRIPTION OF THE INVENTION

Figure 1:
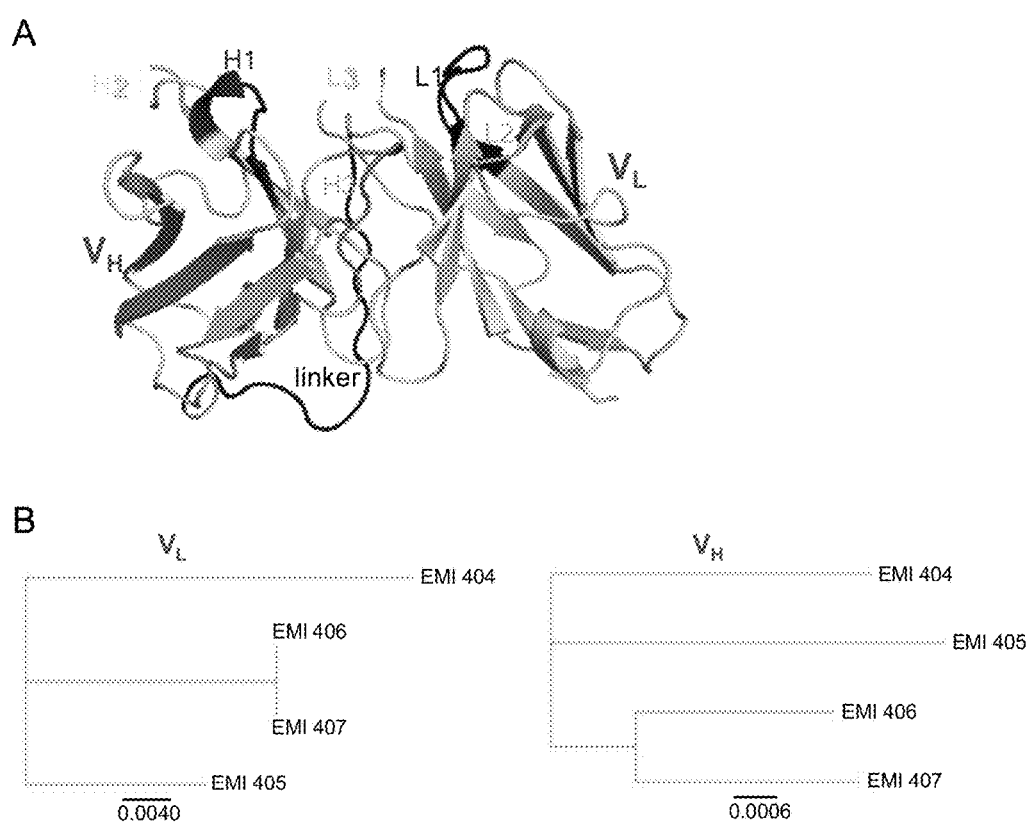
FIG. 1: A. Schematic diagram of the secondary structure of scFv-405. B. Phylogenetic tree based on the neighbor-joining method for light ($V_L$, left) and heavy ($V_H$, right) chain of selected scFv antibody fragments.

The term "internalise" refers to intracellular uptake upon specific binding of the target cell structure.

As used herein, the term "immunotoxin" refers to chimeric molecules in which a cell-binding monoclonal antibody or fragments thereof are chemically coupled or genetically fused to toxins or their subunits. The toxin portion of the immunotoxin can be derived from various sources, such as bacteria, fungi, plants or animals. Toxins of human origin or synthetic toxins (drugs) can be used as well. Immunotoxins as well their construction have been reviewed above and are well known to the person skilled in the art.

As used herein, the term "antibody" refers to polyclonal antibodies, monoclonal antibodies, humanized antibodies, single-chain antibodies, and fragments thereof such as Fab, F(ab')2, Fv, and other fragments which retain the antigen binding function and specificity of the parent antibody.

As used herein, the term "monoclonal antibody" refers to an antibody composition having a homogeneous antibody population. The term is not limited regarding the species or source of the antibody, nor is limited by the manner in which it is made. The term encompasses whole immunoglobulins as well as fragments such as Fab, F(ab')2, Fv, and others, which retain the antigen binding function and specificity of the antibody. Monoclonal antibodies of any mammalian species can be used in this invention. In practice, however, the antibodies will typically be of rat or murine origin because of the availability of rat or murine cell lines for use in making the required hybrid cell lines or hybridomas to produce monoclonal antibodies.

As used herein, the term "human antibodies" means that the framework regions of an immunoglobulin are derived from human immunoglobulin sequences.

As used herein, the term "single chain antibody fragments" (scFv) refers to antibodies prepared by determining the binding domains (both heavy and light chains) of a binding antibody, and supplying a linking moiety, which permits preservation of the binding function. This forms, in essence, a radically abbreviated antibody, having only that part of the variable domain necessary for binding to the antigen. Determination and construction of single chain antibodies are described in U.S. Pat. No. 4,946,778 by Ladner et al.

The term "cytotoxic domain" or "cell-killing domain" may be any toxin known in the art; preferably it is chosen from the following group: ADP-ribosylating enzymes, such as *Pseudomonas* Exotoxin A, Diphtheria-, Cholera-, Pertussis-, Botulinum toxin, etc. (see Carroll S F, Collier R J, Meth. Enzymol. 235, 1994, 631-639), ribosome-inactivating proteins such as Dianthin, Saporin, Bryodin, Gelonin, Ricin, Abrin, Pokeweed Antiviral Protein (PAP), Restrictocin, etc. (see Barbieri L et al. Biochem Biophys. Acta 1154, 1993, 237-282), Rnases, such as Phosphodiesterases, including Bovine seminal RNase, Bovine RNase A, Bovine pancreatic RNase, Angiogenin, Eosinophil-derived Neurotoxin (EDN), Eosinophilic Cationic Protein (ECP), Onconase, Bullfrog Lectin, etc. (see Youle R J et al. Crit. Rev. Therap. Drug Carrier Systems 10, 1993, 1-28), Prodrug-activating enzymes such as Calicheamicin, Glucose Oxidase, Carboxypeptidase, Alkaline Phosphatase, cytosine deaminase, beta-Glucosidase, beta-Glucuronidase, beta-Lactamase, Nitroreductase, Thymidine kinase, Purine nucleoside phosphorylase, etc. (see also Deonarain M P, Epenetos A A, Br. 1. Cancer 70, 1994, 786-794), members of the cathepsin protease family, of the calpains, granzymes, in particular granzym B und granzym M, tumor suppressor-like kinases in particular death-associated protein kinases including DAPK 1 und 2, or microtubule-associated protein (MAP Tau), or any derivative of the above mentioned proteins, or a combination thereof.

Particularly useful is a compound of the invention which is a fusion polypeptide having a cytotoxic domain comprising *Pseudomonas* exotoxin A of the amino acid sequence SEQ ID NO: 43.

The term "detectable label" may be any structural element which can exhibit a measurable parameter for example intrinsically by emission of radiation (radioactivity or by interaction. Detectable labels are fluorescent dyes such as fluorescein, rhodamine, courmarine, and cyanine and derivatives hereof. Preferred fluorophores are emitting in the near infra red (NIR) range between 680 and 950 nm. This wavelength results in very low background fluorescence and excellent tissue penetration and is therefore ideally suited for fluorescence detection in vivo. In a specific embodiment a tumor specific antibody or other ligand in fusion with the Snap-tag is labeled with a BG derivative of a NIR dye. The labeled antibody or ligand serves as an imaging tool that can be used to visualize tumor growth and/or treatment in viva.

In a specific example a BG derivative of a NIR dye emitting at 782 nm was coupled to a single chain antibody fragment SNAP-tag fusion protein targeting EGFR. The resulting in vivo imaging probe was used to detect EGFR expression in a pancreatic carcinoma xenograft model. In other concrete examples several fluorophore coupled complexes AB were used for flow cytometry and confocal microscopy applications. Further the detectable label can be gamma emitting radioisotopes as e.g. iodine-131, lutetium-177, yttrium 90 or any other diagnostically relevant isotope usually combined with a complexing agent as DO-TA or DTAP.

Further the detectable label can be a quantum dot composed of heavy metals like CdSe or InGaP. Quantum dots are favourable optical imaging agents due to their high quantum yield and photostability. Another possibility for a fluorescent label represented by component C may be noble metal nanoclusters composed of a few (8-12) gold or silver atoms, or synthetic fluorophores captured in nanoparticles made from silicon dixode.

Further detectable labels are superparamagnetic iron oxid particles for MRI based molecular imaging.

Fluorescent proteins like GFP or dsRED or derivatives hereof can serve as detectable label coupled to the complexes AB. Fluorescent proteins today cover a wide range of the visible spectrum as well as the near infrared.

Further detectable labels can be enzymes like alkaline phosphatase, peroxidases and galactosidases that are commonly applied in a variety of immunoassays.

The terms "nonpolar amino acids", "polar amino acids", "neutral amino acids", "positive amino acids" as well as "negative amino acids" designate well known properties of both essential and other amino acids. For proteinogenic amino acids the Table 1 summarises these properties:

TABLE 1

| Amino Acid | 3-Letter | 1-Letter | Side-chain polarity | Side-chain charge (pH 7.4) http://en.wikipedia.org/wiki/Amino acid-cite note-Hausman-108 |
|---|---|---|---|---|
| Alanine | Ala | A | nonpolar | neutral |
| Arginine | Arg | R | Basic polar | positive |
| Asparagine | Asn | N | polar | neutral |
| Aspartic acid | Asp | D | acidic polar | negative |
| Cysteine | Cys | C | nonpolar | neutral |
| Glutamic acid | Glu | E | acidic polar | negative |
| Glutamine | Gln | Q | polar | neutral |
| Glycine | Gly | G | nonpolar | neutral |
| Histidine | His | H | Basic polar | positive(10%) neutral(90%) |
| Isoleucine | Ile | I | nonpolar | neutral |
| Leucine | Leu | L | nonpolar | neutral |
| Lysine | Lys | K | Basic polar | positive |
| Methionine | Met | M | nonpolar | neutral |
| Phenylalanine | Phe | F | nonpolar | neutral |
| Proline | Pro | P | nonpolar | neutral |
| Serine | Ser | S | polar | neutral |
| Threonine | Thr | T | polar | neutral |
| Tryptophan | Trp | W | nonpolar | neutral |
| Tyrosine | Tyr | Y | polar | neutral |
| Valine | Val | V | nonpolar | neutral |

Polypeptides show a peptide bond which is used to polymerise single amino acids to the biopolymer. Peptide bonds are subject to an enzymatical degradation by exo- or endopeptidases. In order to increase stability of polypeptides under natural conditions it is possible to block the N-terminal or C-terminal and/or to modify the polypeptide backbone for example by introducing peptide bonds formed by D-amino acids in particular as retro/inverso orientation.

EXAMPLES

Cells and Culturing

The human acute myeloid leukemia M2-derived cell line Kasumi-1 was purchased from the German Resource Centre for Biological Material (DSMZ, Braunschweig, Germany) and used as selection antigen. Cells were cultured in 80% (v/v) RPMI 1640 GlutaMAX-I medium (Invitrogen, Eggenstein, Germany) supplemented with 20% (v/v) fetal calf serum (FCS, Invitrogen) at 37° C. and 5% $CO_2$ and splitted every 3-4 days in a ratio of 1:2. Beside freshly isolated human PBMCs from heparinised full blood using Ficoll reagent (GE Healthcare, München, Germany), the human embryonic kidney cell line HEK293T obtained from the American Type Culture Collection (ATCC, Wesel, Germany) and the KG-1 cell line (DSMZ) were used as negative controls. Cells were grown in 90% (v/v) RPMI 1640 GlutaMAX-I medium containing 10% (v/v) FCS and 1% (v/v) Penicillin/Streptomycin (stock solution of 10,000 units penicillin and 10,000 μg streptomycin/ml, Invitrogen, Germany) using the same conditions as above. Additionally, HEK293T cells were used for transfection and expression of scFv-SNAP-tag fusion proteins. To do so, cells were seeded into 24-well culture plates at a density of $6×10^4$ cells/well and incubated with 1-2 μg plasmid DNA and 3 μl FuGene HD Transfection Reagent (Roche Diagnostics GmbH, Mannheim, Germany) for 48 h. The expression of functional protein and the SNAP-tag activity was tested as previously described[10]. Successfully transfected cells were cultured under Zeocin selection pressure by adding 100 μg/ml Zeocin (InvivoGen, San Diego, Calif., USA) to the standard medium. For the production of large quantities of protein, transfected cells were cultured in triple flasks (Nunc, Langenselbold, Germany) using 200 ml medium. Medium was renewed every 7-8 days.

Soluble scFv SNAP-Tag Fusion Protein Analysis in ELISA and Flow Cytometry

Successfully mutated scFv were cloned into the pMS expression vector for eukaryotic production of soluble SNAP-tag fusion proteins[13]. The cloning procedure, transfection and culturing of HEK293T cells as well as expression, purification and coupling of eukaryotic scFv-SNAP-tag protein to benzyl-guanine (BG)-modified fluorophores were performed as described previously[10]. The functionality of the scFv-SNAP fusion protein was demonstrated by using the crude cell culture supernatant as well as purified protein in an ELISA experiment. To do so, a 96-well microtiter plate was coated overnight at 4° C. with 100 μl of a 1:100 dilution of Kasumi-1 and PBMC membrane fragments. Subsequently, the plate was washed three times with PBS and blocked for 2 h with 2% MPBS, 100 μl/well of the scFv containing cell supernatant was incubated for 1 h shaking at 400 rpm at RT. Unbound protein was washed away with 0.05% PBST and bound scFv were detected using a rabbit anti SNAP-tag polyclonal antibody (A00684, GenScript, Piscataway, N.J., USA) in a concentration of 0.2 μg/ml as primary antibody and a polyclonal goat anti rabbit HRP-labelled antibody (ab6721, Abcam, Cambridge, UK) in a dilution of 1:5,000 as secondary antibody. Finally, 100 μl of freshly prepared ABTS substrate was added to each well and positive binding was evaluated as described above. For quantitative comparison of the binding strength of the scFv-SNAP-tag fusion proteins, 1 μg of IMAC purified protein pre-blocked in 2% MPBS to a total volume of 100 μl was applied in each microtiter plate well and the ELISA procedure was performed as described above. Bound scFv SNAP-tag fusion proteins were detected via their SNAP-tag as described above. For qualitative testing of binding activity of directly labelled scFv clones on whole cells, 1 μg of the eluted scFv protein was incubated for 1 h on ice and under protection from light with $5×10^5$ freshly harvested PBMCs or Kasumi-1 cells that had been washed three times in blocking buffer (PBS containing 0.5% bovine serum albumin, BSA). After two washing steps with PBS in a cell washer, cells were re-suspended in 300 μl blocking buffer and directly used for binding analysis in flow cytometry and internalization analysis. Gating was performed according to physical characteristics in forward and sideward scatter or trypan blue staining in FL-3 to exclude dead cells and debris.

Determination of the Functional Affinity Constant of Selected scFv Antibodies

A modification of the method described by Benedict et al.[14] was used to determine the affinity constants of each selected scFv antibody. The incubation of Kasumi-1 cells with various PBS-dilutions of each Vista Green-labelled scFv-SNAP protein was performed as described above. Concentrations ranged from 0.5 nM-2000 nM to reach a saturation level with increasing scFv SNAP-tag amount. After subtraction of the background fluorescence signal produced by intrinsic cell fluorescence and unspecific binding of scFv SNAP-tag proteins, the geometric mean of the fluorescence intensity for each scFv and applied concentration was calculated. The functional affinity to PBMCs was tested in parallel to proof the specificity.

Internalization Analysis by Flow Cytometry

The internalization behaviour was tested using the Alexa Fluor 647 labelled scFv SNAP-tag fusion proteins in a flow cytometry-based assay: $5 \times 10^5$ Kasumi-1 cells were washed three times with PBS, re-suspended in standard culturing medium and incubated with 1 µg of the scFv protein for 1 h at 37° C. to allow internalization. In parallel, incubation was performed at 4° C. in 1% $NaN_3$ as a reference for non-internalization. After an additional washing step, the surface-bound scFv SNAP proteins were stripped off by the addition of 0.5 ml 0.05% trypsin for 10 min at 37° C. The reaction was stopped by addition of 0.5 ml RPMI+10% FCS and excess trypsin was washed away twice with PBS. The cell pellet was re-suspended in blocking buffer and the samples were analysed using FACSCalibur flow cytometer (BD Biosciences; Heidelberg, Germany). Each sample was normalized to the non-internalization control (0%) and the positive binding signal before trypsin treatment (100%). To detect any residual scFv fusion protein on the cell surface, we added 0.5 µl rabbit anti SNAP-tag polyclonal antibody as a primary antibody and 0.5 µl goat anti rabbit Alexa Fluor 488 polyclonal antibody (A-11009, Invitrogen, Darmstadt, Germany) as a secondary antibody.

Internalization Analysis by Confocal Microscoy

In order to confirm the internalization behaviour of the selected scFv by confocal imaging, the cells were treated as described above and monitored with a TCS SP5 confocal microscope (LEICA Microsystem, Wetzlar, Germany). The Alexa Fluor 647 labelled proteins were excited using a helium-neon laser at 633 nm. Images of fluorophore and transmitted light were merged using LEICA software. For evaluation of cell internalization kinetics, the selected scFv-SNAP fusion proteins were introduced into the OPERA live cell imaging system. To do so, the Alexa Fluor 647 labelled scFv was incubated at 4° C. with the target cell line Kasumi-1. For optimal cell density, 50-100 µl per well of each sample were pipetted in a black 96-well microtiter plate with transparent bottom (µClear, Greiner bio-one, Frickenhausen, Germany) and cells were allowed to settle at 4° C. A kinetic measurement was performed over the course of 12 h in an Opera® microtiter plate imaging reader (Evotec Technologies, Hamburg, Germany).

Construction, Expression and Purification of scFv ETA' Immunotoxin

Recombinant immunotoxins were constructed using the scFv genes from the ELISA-positive phagemid clones. The reverse-mutated scFv inserts were cloned into the pMT ETA' procaryotic expression vector[15] and transformed into E. coli Rosetta 2 (DE3) for high yield expression of scFv-ETA' fusion proteins. The expression of scFv-ETA' immunotoxin was performed under stress conditions in the presence of compatible solutes as described previously[16]. For recovery of the periplasmic fraction, the bacteria cells were sedimented, re-suspended in buffer (75 mM Tris-HCl, 300 mM NaCl, 10% glycerol, 1 tablet protease inhibitor per 50 ml) and sonicated 9×1 min at 70% intensity. The periplasmic fraction was recovered after centrifugation at 30,000×g for 30 min and recombinant immunotoxin was purified in batch procedure using Ni-NTA sepharose (QIAGEN, Hilden, Germany). The flow-through after initial incubation was collected an incubated again twice. The resin was washed once with buffer 1 (50 mM $NaH_2PO_4$, 300 mM NaCl, 20 mM imidazole), twice with buffer 2 (50 mM $NaH_2PO_4$, 300 mM NaCl, 40 mM imidazole) and bound protein was stripped with elution buffer (50 mM $NaH_2PO_4$, 300 mM NaCl, 250 mM imidazole). The eluted protein was finally purified using size exclusion chromatography as described[16] and analyzed as well as quantified using SDS-PAGE. Functional binding activity was confirmed in flow cytometry using the anti-ETA' monoclonal antibody TC-1 (kindly provided by Dr Galloway, Ohio, USA).

Cell Cytotoxic Effect of scFv-ETA' Constructs

Inhibition of cell proliferation was performed as previously described[13, 17, 18]. A serial dilution of the recombinant immunotoxin was distributed in a 96-well microtiter plate starting from 30 ng/µl. After adding $4 \times 10^4$ Kasumi-1 cells in complete medium, the plates were incubated for 72 h under standard culturing conditions. Cell proliferation was assayed as the metabolization of the tetrazolium salt (XTT) to an orange formazan dye, the absorbance of which was measured at 450 nm in an ELISA reader. All measurements were done in triplicate. Each sample was normalized to DMSO-treated positive controls (0%) and untreated cells (100%) to determine $IC_{50}$.

Induction of apoptosis was detected using a caspase-3/7 activity detection kit (Apo-One Homogeneous Caspase-3/7 Assay, Promega, Mannheim, Germany) according to the manufacturer's instructions. To do so, 0.5 ml aliquots at a concentration of $5 \times 10^5$ Kasumi-1 cells were seeded out in 24-well microtiter plates and incubated with 1 µg immunotoxin for 24 h under standard culturing conditions. Samples were analyzed in duplicate and measured in an ELISA reader. Additionally, apoptosis was analyzed via Annexin A5 staining as described previously[19]. Cells were treated as described above and apoptotic cells were stained with annexin A5 eGFP fusion protein-containing HEK293T cell supernatant[19]. After counterstaining of necrotic cells with propidium iodide, samples were measured in flow cytometry using FACSCalibur.

Bioinformatic Analysis of Antibody Variable Regions

The identification and elucidation of complementarity determining regions (CDRs) in the anti-AML scFv antibodies is demonstrated using commonly available Bioinformatics tools and techniques. First, positive binders in monoclonal phage ELISA were prepared for sequencing by extracting the plasmid vectors using the NucleoSpin Plasmid kit (Macherey-Nagel, Düren, Germany) and subsequent insert PCR using the primer LMB3 (5'-CAG GAA ACA GCT ATG AC-3') and fdSEQ1 (5'-GAA TTT TCT GTA TGA GG-3') as described[11]. The cDNA and amino acid sequence was analyzed using the Vector NTI Advance 11 Sequence Analysis Software and Vector NTI AlignX algorithm (Invitrogen), respectively. Unique sequences were then analyzed with V-BASE (V-Base, The database of human antibody genes) and IgBLAST (U.S. National Library of Medicine, National Center for Biotechnology Information) using the Kabat numbering system[20] to determine framework and CDR of the variable heavy ($V_H$) and variable light ($V_L$) chains. SWISS-MODEL[21-23] (Swiss-Model, Biozentrum, The Center for Molecular Life Sciences) was used to model $V_H$ and $V_L$ chain, PyMOL v1.5 was used for computer graphic modeling. Homology of the selected scFv antibodies was modeled in a phylogenetic tree using the Neighbor-Joining algorithm.

Data Analysis

Quantitative analysis of soluble scFv proteins was carried out using the AIDA image analyzer 4.27 software (Raytest, Straubenhardt, Germany) after digital scanning of Coomassie stained SDS polyacrylamide gels. Fluorophorelabelled scFv were detected in the VersaDoc MP System (BIO-Rad, Offenbach, Germany) using the QuantityOne Basic 1-D Analysis software v4.2.1 (BIO-Rad). Data from flow cytometric analysis were evaluated using the CellQuest software (Becton Dickinson, Heidelberg, Germany) and the Windows Multiple Document Interface for Flow Cytometry version 2.8 (WinMDI, Joseph Trotter, USA). Statistical analysis was carried out with GraphPad Prism software (GraphPad, La Jolla, Calif., USA). Data were quoted as mean±standard deviation (SD). A two-tailed t-test was used to determine the significance of independent experiments. The criterion $p<0.05$ was considered significant (*), $p<0.01$ very significant () and $p<0.001$ highly significant (*). Saturation binding curves were generated by non-linear regression using the Levenberg-Marquardt algorithm. $IC_{50}$ of immunotoxin was calculated by non-linear regression using a sigmoidal dose response equation.

Results

Binding of Selected AML-Specific Antibody Fragments on Intact Cells fluorophores Vista Green or Alexa Fluor 647 using BG-SNAP substrates. First, classification of binding strength was carried out based on the measured absorption values in monoclonal scFv-ELISA. To do so, 1 μg of each purified scFv protein was incubated with immobilized membrane fragments of Kasumi-1 and PBMC as negative control. Positive binding was detected using a rabbit anti-SNAP-tag primary antibody and a HRP-labelled goat anti rabbit secondary antibody and visualized after the addition of ABTS. Selected clones with an absorption value at least 2.5 fold higher than the negative controls were classified as moderately binding, while clones with an absorption value more than 5 fold higher were declared highly binding. According to this classification, one of the selected internalizing binders, namely EMI404, revealed high binding activity to Kasumi-1 membrane fragments, the remaining three, namely EMI405, EMI406 and EMI407, showed moderate binding activity (FIG. 2B). Additionally, we assessed the binding strength to viable target cells based on flow cytometric analysis and found a minimum of 67.3% for clone EMI404 and a maximum of 80.2 shifted Kasumi-1 cells in FL-1 for clone EMI406 when incubated with 1 μg Vista Green labelled protein (FIG. 2C). No unspecific binding to PBMC or other negative control cells such as HEK293T was observed at any time. The $K_D$ values were determined by

| Seq. ID NO | Clone | incidence | scFv phage binder | | scFv SNAP fusion binder | | Affinity | Internalization | |
|---|---|---|---|---|---|---|---|---|---|
| | | | ELISA | FACS | ELISA | FACS | $K_D \pm$ SD in nM | FACS | Confocal |
| 37 | EMI404 | 1x | ++ | ++ | ++ | ++ | 62.9 ± 6.8 | ++ | + |
| 38 | EMI405 | 8x | + | ++ | + | ++ | 63.9 ± 8.3 | ++ | ++ |
| 39 | EMI406 | 13x | + | ++ | + | ++ | 159.4 ± 87.5 | ++ | ++ |
| 40 | EMI407 | 3x | + | + | + | ++ | 404.4 ± 183.0 | + | ++ |

Selected binders are categorized as moderate (+) or strong (++) based on the ELISA absorption value (+ < 5x, ++ > 5x higher than background), the percentage of shifted cells identified by FACS (+ < 60%, ++ > 60%) and the fluorescence intensity under confocal microscopy (+ high, ++ very high). Experiments were carried out at least three times.

Selected binders are categorized as moderate (+) or strong (++) based on the ELISA absorption value (+<5x, ++>5x higher than background), the percentage of shifted cells identified by FACS (+<60%, ++>60%) and the fluorescence intensity under confocal microscopy (+high, ++very high). Experiments were carried out at least three times.

FIG. 1: A. Schematic diagram of the secondary structure of scFv-405. The orientation of the represented scFv is $V_H$-linker-$V_L$. The heavy ($V_H$) and light chain (Vl) are depicted in grey, the CDRs of $V_H$ are highlighted in warm colors (H1: red, H2: yellow, H3: orange), the CDRs of $V_L$ in cold colors (L1: dark blue, L2: green, L3: light blue). The CDRs are defined according to Kabat numbering system. The connecting $(Gly_4Ser)_3$ linker is display in black. B. Phylogenetic tree based on the neighbor-joining method for light ($V_L$, left) and heavy ($V_H$, right) chain of selected scFv antibody fragments. The lateral distance (scale bar) is proportional to their sequence homology.

Binding Affinity of Soluble scFv-SNAP-Tag Proteins

The reverse-mutated scFv inserts were cloned into the bicistronic pMS SNAP-tag eukaryotic expression vector to generate scFv-SNAP-tag fusion proteins of the selected binders (FIG. 2A) after transfection into HEK293T cells. Effective transfection was realized by selection with Zeocin and enhanced green fluorescent (eGFP) protein activity in fluorescence microscopy. The scFv-SNAP-tag fusion proteins were secreted into the supernatant, purified via IMAC and analysed by SDS-PAGE and Western blot. The purified proteins were either used directly or after coupling to the incubating Kasumi-1 cells with up to 2000 nM of each binder to reach a saturation level. The increasing MFIs of cell-bound scFv were measured, normalized to background fluorescence and plotted against the applied scFv concentrations in a saturation-binding curve. The calculated $K_D$ values of each sample using non-linear regression ranged from 62.9±26.8 nM for clone EMI404 to 404.4±183.0 nM for clone EMI407 (Tab. 2). All experiments were at least repeated three times.

Figure 2:
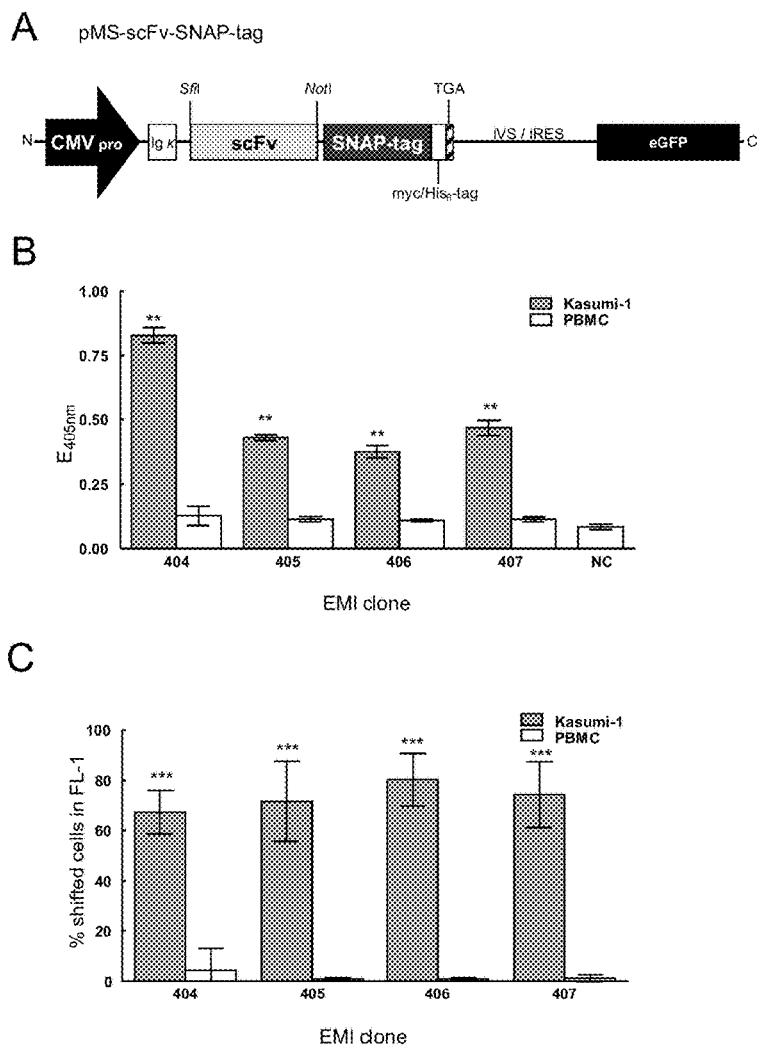
FIG. 2: Construction and binding analysis of purified scFv-SNAP-tag fusion proteins.

FIG. 2. Construction and binding analysis of purified scFv-SNAP-tag fusion proteins. A. Schematic diagram of the bicistronic eukaryotic expression cassette for the recombinant SNAP-tag fusion proteins. Under the control of the cytomegalovirus promoter (CMV pro), the pMS scFv-SNAP vector encodes the antigen binding domain (scFv) joined in-frame to the SNAP-tag. The immunoglobulin kappa leader sequence (Ig κ) upstream of the scFv SNAP-tag fusion leads to the secretion of fusion proteins into the supernatant, and a TGA stop codon is placed immediately after the C-terminal $His_6$-tag. The additionally transcribed internal ribosome entry site (IVS-IRES) mediates the cotranslational expression of enhanced fluorescent protein (eGFP). B. Binding analysis of scFv SNAP-tag fusion proteins in monoclonal scFv ELISA on functional membrane fragments. Tumor binding activity to AML-derived Kasumi-1 cells (grey bars) was compared to healthy peripheral blood mononuclear cells (PBMC, white bars). C. Flow cytometric binding analysis of fluorophor-labelled scFv-SNAP-tag proteins on Kasumi-1 (grey bars) and PBMC (white bars) cells. After subtraction of background fluorescence, the percentage of fusion protein binding was detected in the FL-1 channel (488 nm). NC: negative controls. The stars indicate a significant difference relative to the PBMC controls.

Internalization Behavior

The Alexa Fluor 647 labelled scFv SNAP-tag fusion proteins were incubated with the target cells at 37° C. for 1 h to allow internalization. After having confirmed functional binding activity by flow cytometry, surface-bound scFv proteins were stripped using trypsin elution and the fluorescent profile was checked once more. The clones EMI404, 405, 406 and 407 still showed a significant fluorescent signal in FL-4 generated by endocytosed scFv fusion proteins. In contrast, a signal was neither detected after trypsin elution when incubation was carried out at 4° C. nor when the target cells were incubated with the unspecific 425(scFv)-SNAP fusion protein (FIG. 3A). Normalizing the signal after trypsin treatment to the signal before surface bound scFv were eluted, 68.7 f 3.5% of clone EMI404, 66.2±9.9% of clone EMI405, 65.5±20.4% of clone EMI406 and 11.8±6.3% of clone EMI407 were internalized after 1 h incubation at 37° C. (FIG. 3B). Analysis was repeated three times. No surface bound scFv SNAP-tag protein could be detected via secondary anti SNAP-tag antibody after trypsin elution. Using this approach, we confirmed that surface-bound scFv was efficiently eluted and that the detected fluorescence signal must be due to internalized scFv protein.

Figure 3:
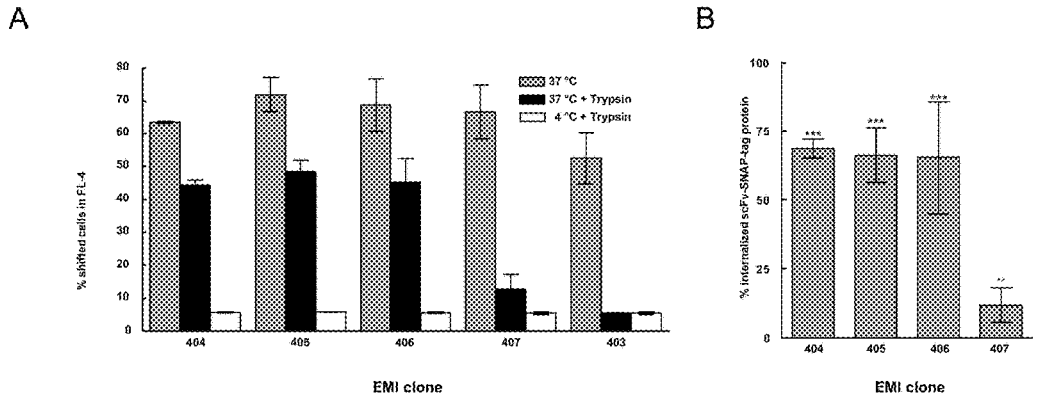
FIG. 3: Internalization of scFv-SNAP-tag fusion proteins.

FIG. 3. Internalization of scFv-SNAP-tag fusion proteins. A. Flow cytometry-based scFv-SNAP internalization assay. Alexa Fluor 647 dye-labelled scFv-SNAP-tag fusion proteins were incubated with Kasumi-1 cells and fluorescence signal was measured in the FL-4 channel (grey bars). After trypsin elution of surface bound proteins, maintained fluorescence signal was observed when incubation was performed at 37° C. (black bars), indicating internalized scFv fusion protein. When incubated at 4° C. no fluorescence signal could be detected after trypsin elution (white bars) B. Relative amount of internalized scFv fusion protein after 60 min incubation at 37° C. Flourescence signal after elution of surface bound scFv constructs was related to the signal before trypsin elution. The stars indicate a significant difference relative to the incubation at 4° C.

As an example, the internalization pattern of clone EMI405 was monitored by confocal microscopy. The labelled scFv protein bound specifically to Kasumi-1 cells and was internalized under the same condition as described before, while unspecific 425(scFv)-SNAP showed no fluorescence signal. However, incubation at 4° C. inhibited the internalization into the cytosol (FIG. 4A). Additionally, clones showing internalizing behavior in FACS analysis were checked for their internalization kinetics in the Opera live cell imager and cellular uptake within the first 15 min incubation at 37° C. was observed (FIG. 4B).

Figure 4:
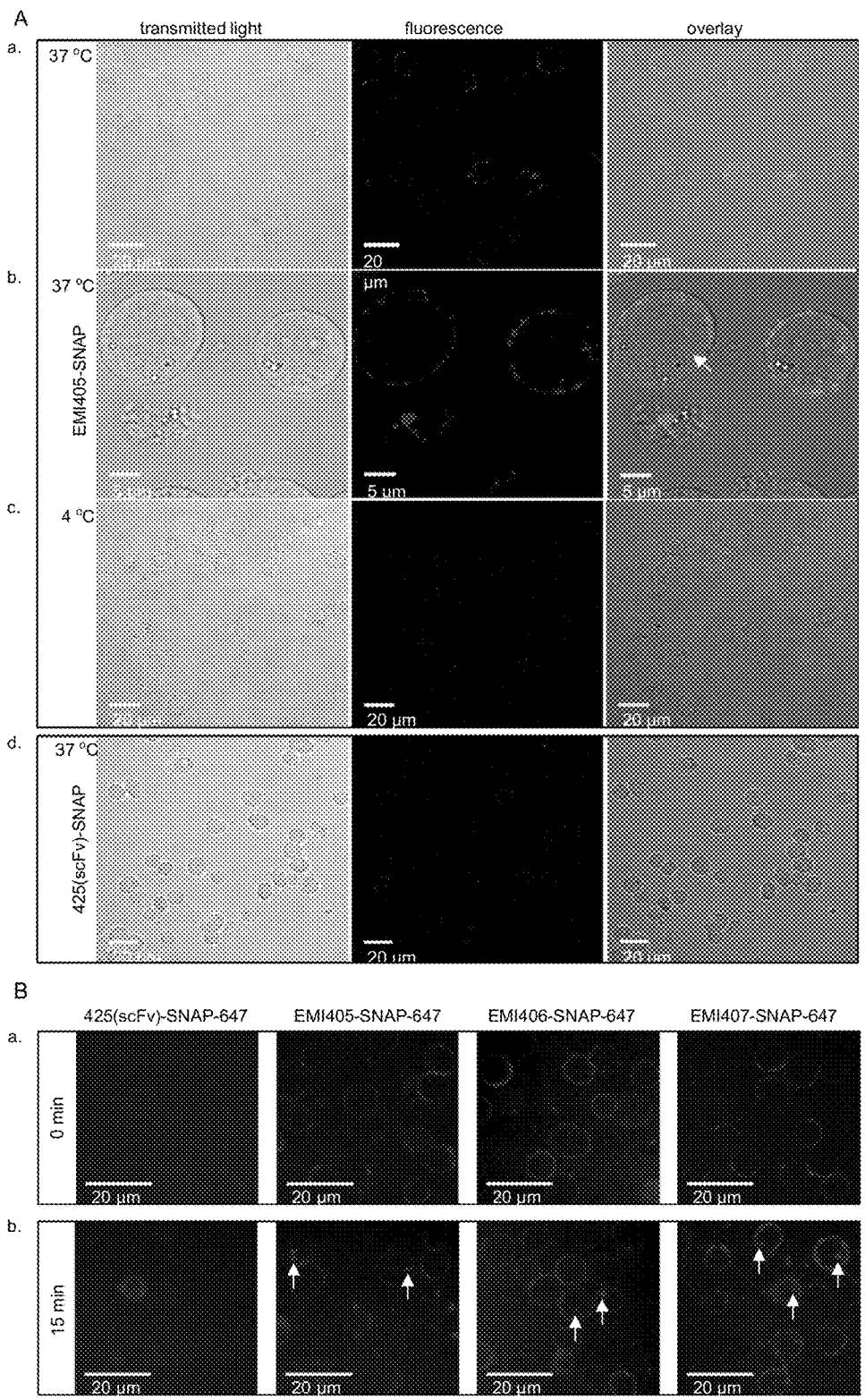
FIG. 4: Binding and internalization of scFv-SNAP-tag fusion proteins by confocal microscopy.

FIG. 4. Binding and internalization of scFv-SNAP-tag fusion proteins by confocal microscopy.

A. Confocal images were obtained for the Kasumi-1 cell line. Cells were incubated with 1 μg EMI405(scFv)-SNAP-647 for 60 min at 37° C. (a+b) or at 4° C. (c). Surface bound proteins were eluted with trypsin to detect internalized scFv protein. As a negative control, the Kasumi-1 cells were incubated with the irrelevant 425(scFv)-SNAP at 37° C. (d). Magnification is indicated by the white scale bars.

B. The internalization kinetics were observed in a live cell imager. Kasumi-1 cells revealed a corona-shaped fluorescent signal when incubated with EMI405, EMI406 and EMI407 at time point 0 min (a). The cellular uptake was observed after 15 min incubation (b.) under physiologic conditions indicated by intracellular fluorescent vesikels (white arrows).

Cytotoxicity of Recombinant Immunotoxin

After verification of internalizing behavior of scFv EMI405 SNAP fusion protein in flow cytometry and confocal microscopy, the scFv insert was transferred to the pMT ETA' prokaryotic expression vector to generate scFv-ETA' fusion proteins (FIG. 5A). The immunotoxin was successfully produced, purified to 90% and analyzed for functional binding activity in flow cytometry (data not shown). Its specific binding was confirmed by flow cytometry after incubating the target cell line Kasumi-1 with increasing amounts of the immunotoxin (FIG. 5B). Its cytotoxic effect was evaluated based on a colorimetric XTT cell proliferation assay using the target cell line Kasumi-1 and KG-1 as negative control and compared to the effect of the unspecific 425(scFv)-ETA' on both cells. We observed a dose dependent inhibition of cell growth with an $IC_{50}$ value of 265.2±0.2 nM for EMI405(scFv)-ETA' (FIG. 5C). By contrast, the cell viability of Kasumi-1 cells was neither affected by the unspecific 425(scFv)-ETA', nor by the non-internalizing scFv EMI408. Moreover, scFv EMI405 had no impact on the cell viability of the negative control cells KG-1, demonstrating the exclusive toxicity to the target cells.

Figure 5:
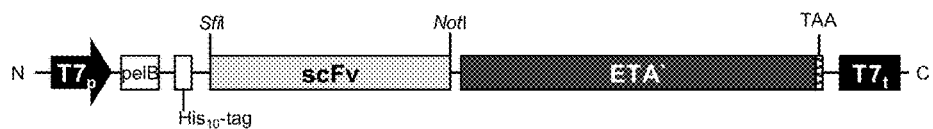
FIG. 5: Construction and cell viability impact of EMI405 (scFv)-ETA' fusion proteins.
Figure 5:
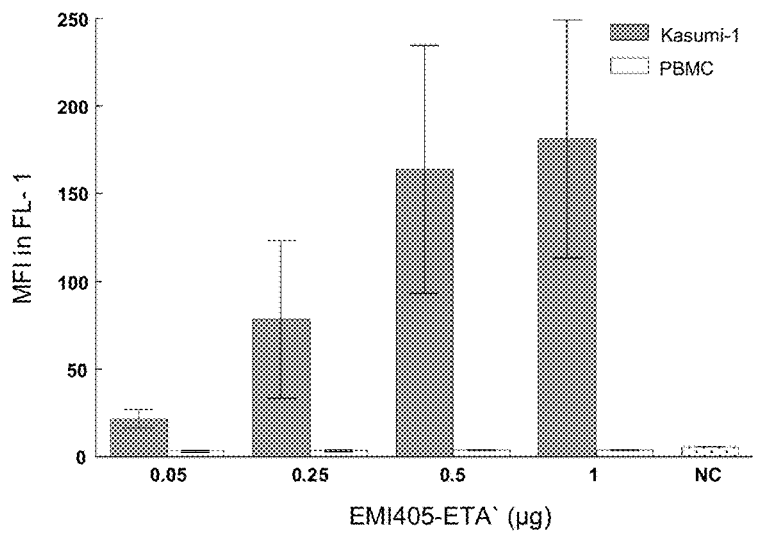
Figure 5:
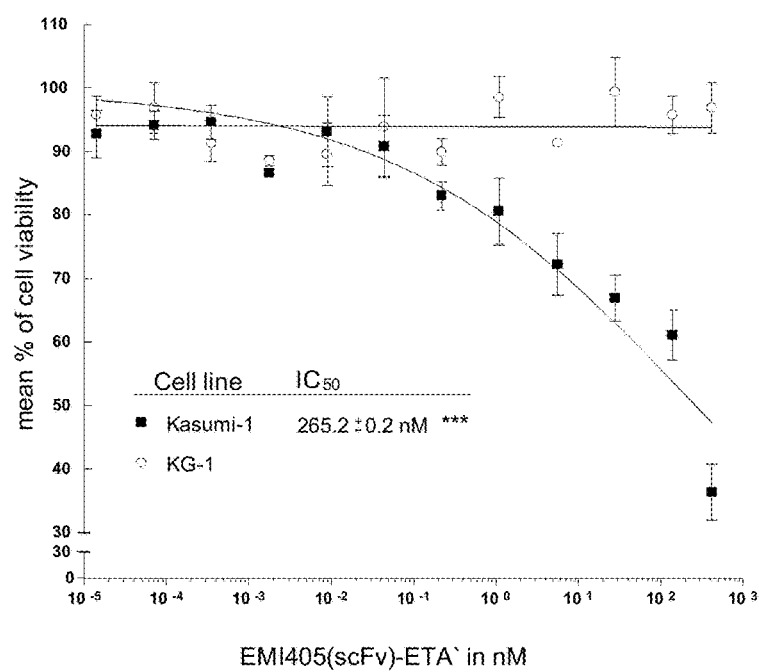

FIG. 5. Construction and cell viability impact of EMI405 (scFv)-ETA' fusion protein (SEQ ID NO: 43).

A. Schematic diagram of the pET-derived expression cassette. Under the transcriptional control of the T7 promoter ($T7_p$) and T7 terminator sequence ($T7_t$), the pMT-scFv-vector encodes the phage display-selected scFv, joined in-frame to a truncated variant of Pseudomonas exotoxin A (ETA'). The fusion protein is expressed with a N-terminal deca-histidine tag (Hisao) and translocated into the periplasmic space of E. coli by the pectate lyase B (pelB) signal peptide. The stop codon TAA is generated immediately after the C-terminal ETA' domain.

B. Flow cytometry-based determination of dose-dependent binding activity. Kasumi-1 cells were incubated with increasing amounts (14 fM-420 nM) of EMI405(scFv)-ETA' fusion protein. Surface bound molecules were detected (FL-1) via the anti-ETA' monoclonal antibody TC-1 and their mean fluorescence intensity (MFI) was measured in the FL-1 channel in three independent experiments.

C. XTT cell proliferation assays were carried out using the EMI405(scFv)-ETA'. The cytotoxicity of the fusion protein EMI405(scFv)-ETA' against Kasumi-1 cells was determined (■). The non bound KG-1 cell line was used as a negative control (°). The percentage of viable cells was calculated after incubation with PBS (100% viability) and DMSO (0% viability). The half maximal inhibitory concentration ($IC_{50}$) was determined by non-linear regression analysis (sigmoidal dose response).

Detection of Apoptosis

Apoptosis was analyzed by labelling the cells with annexin A5-eGFP and propidium iodide. We could show a time dependent increase of bound annexin A5 exclusively on Kasumi-1 cells after 24 h exposure to the immunotoxin EMI405(scFv)-ETA'. The non-specific 425(scFv)-ETA' construct had no impact on Kasumi-1 (FIG. 6A). Additionally, the caspase-3/7 activity after immunotoxin incubation was examined for 24, 48, 72 and 96 h. The signal of metabolized profluorescent caspase substrate in Kasumi-1 samples was measured and compared to the KG-1 negative control cells. After 96 h, it has been found 33.0±1.4% Kasumi-1 cells but only 0.6±0.1% of the negative cell line KG-1 to be apoptotic ($p<0.0001$). The percentage of apoptotic Kasumi-1 cells was 15.9±0.6% after 72 h and 4.2 f 2.1% after 48 h indicating a time dependent increase when incubated with the same amount of immunotoxin (FIG. 6B). The addition of PBS or the unspecific 425(scFv)-ETA had no impact on cell viability (data not shown). Experiments were repeated twice.

Figure 6:
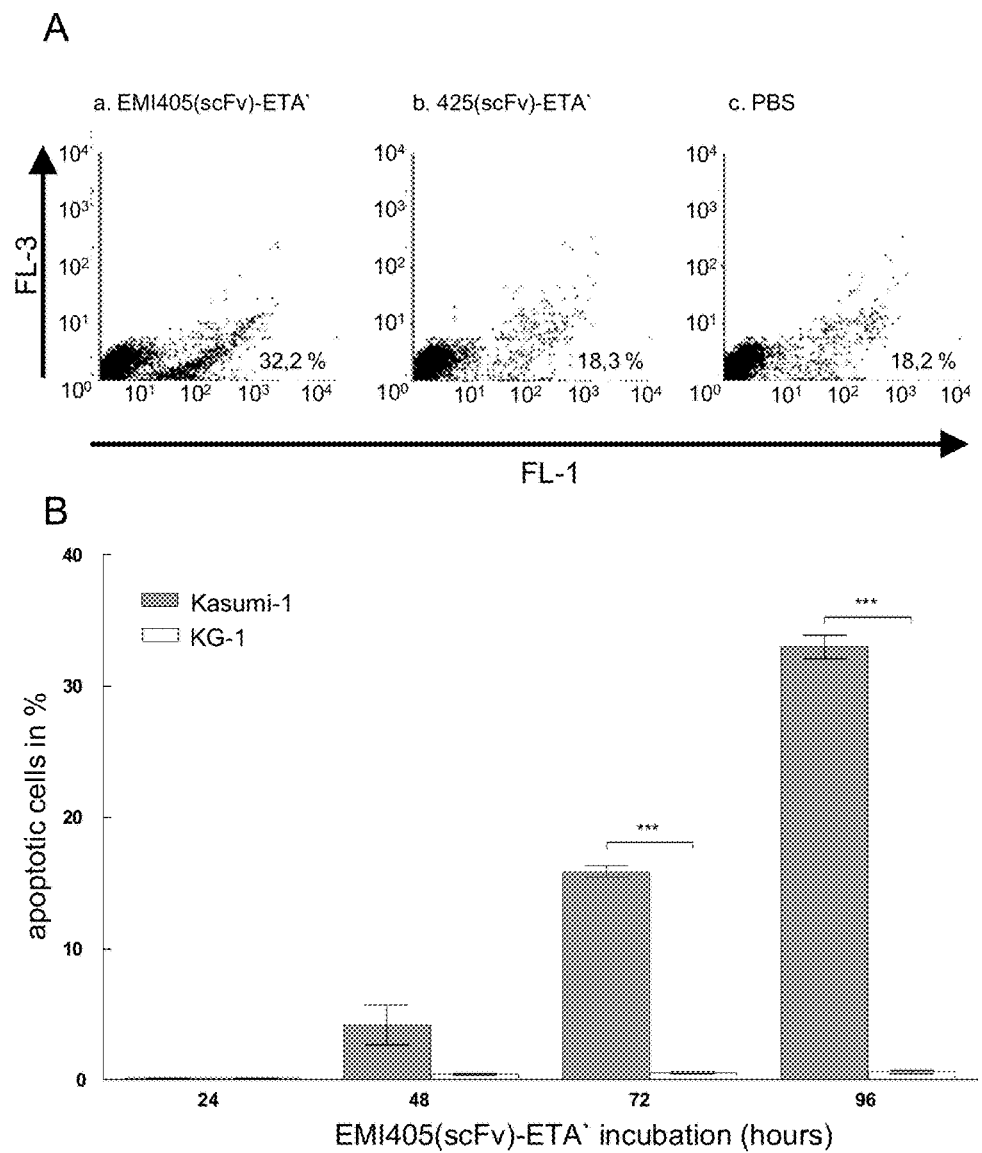
FIG. 6: Apoptosis analysis of the recombinant EMI405 (scFv)-ETA' immunotoxin fusion protein.

FIG. 6. Apoptosis analysis of the recombinant EMI405 (scFv)-ETA' immunotoxin fusion protein.

(A) Flow cytometry-based detection of apoptotic cells using Annexin V-FITC/PI double-staining. Kasumi-1 cells were treated with 1 µg EMI405(scFv)-ETA'(a.), non binding 425(scFv)-ETA' (b.) and PBS (c.) and analyzed after 24 h of incubation. Viable cells are shown in the lower left quadrant, early apoptotic cells in the lower right quadrant and late apoptotic/necrotic cells in the upper right quadrant.

(B) Bar diagram shows percent apoptosis based on activation of caspases-3/7 in Kasumi-1 target (grey bars) and KG-1 control (white bars) cells. Cells were treated with 1 µg EMI405(scFv)-ETA' for up to 96 h. Results are displayed after subtraction of background level when incubated with PBS. ***: highly significant

REFERENCES (1) Abutalib, S. A., and Tallman, M. S. (2006) Monoclonal antibodies for the treatment of acute myeloid leukemia. *Curr Pharm Biotechnol* 7, 343-69.

(2) American Cancer Society Cancer Facts & Figures 2013. http://www.cancer.org/acs/groups/content/@epidemiologysurveilance/document s/document/acspc-036845.pdf. Accession date: 2013

(3) Stone, R. M. (2002) The difficult problem of acute myeloid leukemia in the older adult. *CA Cancer J Clin* 52, 363-71.

(4) Mulford, D. (2008) Antibody therapy for acute myeloid leukemia. *Semin Hematol* 45, 104-9.

(5) Pagel, J. M., Gooley, T. A., Rajendran, J., Fisher, D. R., Wilson, W. A., Sandmaier, B. M., Matthews, D. C., Deeg, H. J., Gopal, A. K., Martin, P. J., Storb, R. F., Press, O. W., and Appelbaum, F. R. (2009) Allogeneic hematopoietic cell transplantation after conditioning with 131I-anti-CD45 antibody plus fludarabine and low-dose total body irradiation for elderly patients with advanced acute myeloid leukemia or high-risk myelodysplastic syndrome. *Blood* 114, 5444-53.

(6) Bunjes, D., Buchmann, I., Duncker, C., Seitz, U., Kotzerke, J., Wiesneth, M., Dohr, D., Stefanic, M., Buck, A., Harsdorf, S. V., Glatting, G., Grimminger, W., Karakas, T., Munzert, G., Dohner, H., Bergmann, L., and Reske, S. N. (2001) Rhenium 188-labeled anti-CD66 (a, b, c, e) monoclonal antibody to intensify the conditioning regimen prior to stem cell transplantation for patients with high-risk acute myeloid leukemia or myelodysplastic syndrome: results of a phase I-II study. *Blood* 98, 565-72.

(7) ten Cate, B., Bremer, E., de Bruyn, M., Bijma, T., Samplonius, D., Schwemmlein, M., Huls, G., Fey, G., and Helfrich, W. (2009) A novel AML-selective TRAIL fusion protein that is superior to Gemtuzumab Ozogamicin in terms of in vitro selectivity, activity and stability. *Leukemia* 23, 1389-97.

(8) Pfizer Voluntarily Withdraws Cancer Treatment Mylotarg from U.S. Market. http://www.fda.gov/NewsEvents/Newsroom/PressAnnouncements/ucm216448.ht m. Accession date: Nov. 10, 2011

(9) Frankel, A. E., Sievers, E. L., and Scheinberg, D. A. (2000) Cell surface receptor-targeted therapy of acute myeloid leukemia: a review. *Cancer Blather Radiopharm* 15, 459-76.

(10) Kampmeier, F., Ribbert, M., Nachreiner, T., Dembski, S., Beaufils, F., Brecht, A., and Barth, S. (2009) Site-Specific, Covalent Labeling of Recombinant Antibody Fragments via Fusion to an Engineered Version of 6-O-Alkylguanine DNA Alkyltransferase. *Bioconjug Chem* 20, 1010-5.

(11) Fitting, J., Killian, D., Junghanss, C., Willenbrock, S., Murua Escobar, H., Lange, S., Nolte, I., Barth, S., and Tur, M. K. (2011) Generation of recombinant antibody fragments that target canine dendritic cells by phage display technology. *Vet Comp Oncol* 9, 183-95.

(12) Tur, M. K., Rothe, A., Huhn, M., Goerres, U., Klimka, A., Stocker, M., Engert, A., Fischer, R., Finner, R., and Barth, S. (2003) A novel approach for immunization, screening and characterization of selected scFv libraries using membrane fractions of tumor cells. *Int J Mol Med* 11, 523-7.

(13) Stocker, M., Tur, M. K., Sasse, S., Krussmann, A., Barth, S., and Engert, A. (2003) Secretion of functional anti-CD30-angiogenin immunotoxins into the supernatant of transfected 293T-cells. *Protein Expr Purif* 28, 211-9.

(14) Benedict, C. A., MacKrell, A. J., and Anderson, W. F. (1997) Determination of the binding affinity of an anti-CD34 single-chain antibody using a novel, flow cytometry based assay. *J Immunol Methods* 201, 223-31.

(15) Tur, M. K., Huhn, M., Thepen, T., Stocker, M., Krohn, R., Vogel, S., Jost, E., Osieka, R., van de Winkel, J. G., Fischer, R., Finnern, R., and Barth, S. (2003) Recombinant CD64-specific single chain immunotoxin exhibits specific cytotoxicity against acute myeloid leukemia cells. *Cancer Res* 63, 8414-9.

(16) Tur, M. K., Huhn, M., Jost, E., Thepen, T., Brummendorf, T. H., and Barth, S. (2011) In vivo efficacy of the recombinant anti-CD64 immunotoxin H22(scFv)-ETA' in a human acute myeloid leukemia xenograft tumor model. *Int J Cancer* 129, 1277-82.

(17) Barth, S., Huhn, M., Matthey, B., Klimka, A., Galinski, E. A., and Engert, A. (2000) Compatible-solute-supported periplasmic expression of functional recombinant proteins under stress conditions. *Appl Environ Microbiol* 66, 1572-9.

(18) Barth, S., Huhn, M., Matthey, B., Tawadros, S., Schnell, R., Schinkothe, T., Diehl, V., and Engert, A. (2000) Ki-4(scFv)-ETA', a new recombinant anti-CD30 immunotoxin with highly specific cytotoxic activity against disseminated Hodgkin tumors in SCID mice. *Blood* 95, 3909-14.

(19) Tur, M. K., Neef, I., Jager, G., Teubner, A., Stocker, M., Melmer, G., and Barth, S. (2009) Immunokinases, a novel class of immunotherapeutics for targeted cancer therapy. *Curr Pharm Des* 15, 2693-9.

(20) Kabat, E. A., and Wu, T. T. (1991) Identical V region amino acid sequences and segments of sequences in antibodies of different specificities. Relative contributions of VH and VL genes, minigenes, and complementarity-determining regions to binding of antibody-combining sites. *J Immunol* 147, 1709-19.

(21) Arnold, K., Bordoli, L., Kopp, J., and Schwede, T. (2006) The SWISS-MODEL workspace: a web-based environment for protein structure homology modelling. *Bioinformatics* 22, 195-201.

(22) Schwede, T., Kopp, J., Guex, N., and Peitsch, M. C. (2003) SWISS-MODEL: An automated protein homology-modeling server. *Nucleic Acids Res* 31, 3381-5.

(23) Guex, N., and Peitsch, M. C. (1997) SWISS-MODEL and the SwissPdbViewer: an environment for comparative protein modeling. *Electrophoresis* 18, 2714-23.

(24) Chothia, C., and Lesk, A. M. (1987) Canonical structures for the hypervariable regions of immunoglobulins. *J Mol Biol* 196, 901-17.

(25) Chothia, C., Lesk, A. M., Tramontano, A., Levitt, M., Smith-Gill, S. 1, Air, G., Sheriff, S., Padlan, E. A., Davies, D., Tulip, W. R., and et al. (1989) Conformations of immunoglobulin hypervariable regions. *Nature* 342, 877-83.

(26) Stone, R. M., O'Donnell, M. R., and Sekeres, M. A. (2004) Acute myeloid leukemia. *Hematology Am Soc Hematol Educ Program*, 98-117.

(27) Tallman, M. S. (2005) New strategies for the treatment of acute myeloid leukemia including antibodies and other novel agents. *Hematology Am Soc Hematol Educ Program*, 143-50.

(28) Khandare, J. J., and Minko, T. (2006) Antibodies and peptides in cancer therapy. *Crit Rev Ther Drug Carrier Syst* 23, 401-35.

(29) Becerril, B., Paul, M. A., and Marks, J. D. (1999) Toward selection of internalizing antibodies from phage libraries. *Biochem Biophys Res Commun* 255, 386-93.

(30) Barth, S., Winkler, U., Diehl, V., and Engert, A. (1997) [Immunotoxins. Mechanism of action and applications in malignant diseases]. *Internist (Berl)* 38, 1063-9.

(31) Hetzel, C., Bachran, C., Tur, M. K., Fuchs, H., and Stocker, M. (2009) Improved immunotoxins with novel functional elements. *Curr Pharm Des* 15, 2700-11.

(32) Stish, B. J., Chen, H., Shu, Y., Panoskaltsis-Mortari, A., and Vallera, D. A. (2007) Increasing anticarcinoma activity of an anti-erbB2 recombinant immunotoxin by the addition of an anti-EpCAM sFv. *Clin Cancer Res* 13, 3058-67.

(33) Schmidt, M. M., Thurber, G. M., and Wittrup, K. D. (2008) Kinetics of anticarcinoembryonic antigen antibody internalization: effects of affinity, bivalency, and stability. *Cancer Immunol Immunother* 57, 1879-90.

(34) Hetzel, C., Bachran, C., Fischer, R., Fuchs, H., Barth, S., and Stocker, M. (2008) Small cleavable adapters enhance the specific cytotoxicity of a humanized immunotoxin directed against CD64-positive cells. *J Immunother* 31, 370-6.

(35) Stahnke, B., Thepen, T., Stocker, M., Rosinke, R., Jost, E., Fischer, R., Tur, M. K., and Barth, S. (2008) Granzyme B-H22(scFv), a human immunotoxin targeting CD64 in acute myeloid leukemia of monocytic subtypes. *Mol Cancer Ther* 7, 2924-32.

The invention claimed is:
1. A compound comprising:
   a domain comprising a polypeptide which binds to the surface of AML blast cells and is internalised upon binding to the AML blast cells, and
   a cytotoxic domain;
   wherein the compound is a fusion polypeptide with the amino acid sequence of SEQ ID NO: 43.

2. A pharmaceutical composition comprising the compound of claim 1.

* * * * *